US008652524B2

(12) United States Patent
Ono et al.

(10) Patent No.: US 8,652,524 B2
(45) Date of Patent: Feb. 18, 2014

(54) ORGAN REGENERATION DEVICE

(75) Inventors: Ichiro Ono, Hokkaido (JP); Yoshikiyo Akasaka, Tokyo (JP); Takehiko Nakajima, Ibaragi (JP)

(73) Assignees: Ichiro Ono, Hokkaldo (JP); Yoshikiyo Akasaka, Tokyo (JP); Hoya Technosurgical Corporation, Tokyo (JP)

( * ) Notice: Subject to any disclaimer, the term of this patent is extended or adjusted under 35 U.S.C. 154(b) by 371 days.

(21) Appl. No.: 12/325,015

(22) Filed: Nov. 28, 2008

(65) Prior Publication Data

US 2009/0142403 A1 Jun. 4, 2009

(30) Foreign Application Priority Data

Nov. 30, 2007 (JP) ................................. 2007-311777

(51) Int. Cl.
*A61K 9/14* (2006.01)
*A61K 47/42* (2006.01)
*A61K 47/02* (2006.01)
*A61K 31/7088* (2006.01)
*A61K 38/18* (2006.01)
*A61K 35/12* (2006.01)

(52) U.S. Cl.
USPC ............. 424/489; 514/773; 514/769; 514/44; 514/12; 424/93.7

(58) Field of Classification Search
None
See application file for complete search history.

(56) References Cited

U.S. PATENT DOCUMENTS 5,934,287 A * 8/1999 Hayashi et al. ............... 128/898
2005/0255320 A1 * 11/2005 Noguchi ....................... 428/403

FOREIGN PATENT DOCUMENTS

JP 2004-123610 4/2004

OTHER PUBLICATIONS

Li et al (Biomaterials. 2006; 27: 3115-3124).*
Chung et al (Journal of Controlled Release. Jun. 2007; 121: 91-99).*
Cheng et al (Materials Science and Engineering. 2005; C25:541-547).*
Leonelli et al (J. Am. Ceram. Soc. 2002; 85(2):487-489).*
Leonelli et al. (Journal of Non-Crystalline Solids. 2003; 316: 198-216).*
Zhang et al (Materials Letters. 2004; 58: 719-722).*
S.A. Eming et al., "Gene Transfer in Tissue Repair: Status, Challenges and Future Directions", Expert Opinion Biol. Ther., 2004, vol. 4, No. 9, pp. 1373-1386.
K. A. Holbrook et al., "Expression of Morphogens During Human Follicle Development In Vivo and a Model for Studying Follicle Morphogenesis In Vitro", The Journal of Investigative Dermatology, 1993, vol. 101, No. 1, Suppl., pp. 39S-48S.
M. Kobune et al., "Wnt3/RhoA/ROCK Signaling Pathway is Involved in Adhesion-Mediated Drug Resistance of Multiple Myeloma in an Autocrine Mechanism", Mol. Cancer Ther., 2007, vol. 6, No. 6, pp. 1774-1784.
Japanese Office Action issued with respect to Japanese Patent Application No. 2007-311777, dated Nov. 14, 2012, with English translation thereof.

* cited by examiner

*Primary Examiner* — Scott Long
(74) *Attorney, Agent, or Firm* — Greenblum & Bernstein, P.L.C.

(57) ABSTRACT

An organ regeneration device adapted to be used by placing it into a defective portion of an organ to regenerate the organ is provided. The organ regeneration device has a base body having a shape corresponding to a shape of the defective portion of the organ. The organ regeneration device also has particles carried on the base body, wherein the particles are composed of a different material from that of the base body. The organ regeneration device also has a growth-related substance contained in the organ regeneration device for growth and differentiation of cells around the defective portion. The growth-related substance contains an angiogenesis factor. Further, the growth-related substance contains nucleic acid containing a base sequence coding for amino-acid sequence of a growth factor different from the angiogenesis factor. Furthermore, the nucleic acid is introduced into a host cell.

22 Claims, 10 Drawing Sheets

ORGAN REGENERATION DEVICE

FIELD OF THE INVENTION

The present invention relates to an organ regeneration device.

BACKGROUND ART

The cascade of wound healing is involved by various growth factors, and proceeds by a combination of two mechanisms which include regeneration and repair. In the case of humans, the cascade of wound healing proceeds mainly by a repair mechanism.

According to recent findings about tissue regeneration, it has come to be believed that a family of growth factors called morphogens play important roles in tissue regeneration. More specifically, it has become apparent that, in wound healing as well as in tissue development in fetal life, there is a possibility that individual cells are widely involved in tissue formation and regeneration depending on the local expression levels of morphogens.

Further, there are also findings that various tissues can be regenerated by modification of stem cells in an in vitro environment. Based on such findings, it has recently come to be believed that an organ as well as tissue can be regenerated by, for example, stimulating tissue stem cells with various morphogens in an in situ environment. More specifically, it has come to be believed that differentiation of tissue stem cells into, for example, skin appendages can be induced by such a method as described above (see, for example, Eming et al., Expert Opin Biol Ther, 4, 1373-1386, 2004).

As described above, in organ regeneration, various growth factors are involved in the growth and differentiation of cells. Therefore, it can be considered that organ regeneration can be realized by implanting, into a defective portion of an organ, a biomaterial designed to allow these growth factors to promote the growth and differentiation of cells.

In order to regenerate a defective portion of an organ using such a biomaterial as described above to restore the organ to a state closer to its normal state, it is important to supply growth factors in proper concentrations at proper timings. In the case where an organ to be regenerated is, for example, skin, in order to induce regeneration of pilosebaceous units including hair follicles and sebaceous glands being skin appendages, it is necessary to supply two or more growth factors associated with the regeneration of these appendages. Therefore, a biomaterial (implant) designed to be able to supply two or more growth factors is required to skillfully control various factors, such as a site where a growth factor is to be supplied, the concentration of the growth factor at the site, and the timing of supply of the growth factor, for each of the growth factors.

However, a biomaterial capable of supplying various growth factors while controlling such various factors as described above for each of the growth factors has not yet been developed. That is, current technology has not yet reached a level where a defective organ such as skin can be restored to its normal state.

SUMMARY OF THE INVENTION

It is an object of the present invention to provide an organ regeneration device capable of regenerating a defective portion of an organ to restore the organ to its normal state.

These objects are achieved by the present inventions (1) to (21) described below.

(1) An organ regeneration device for regenerating a defective portion of an organ, the organ regeneration device being adapted to be used by placing it into the defective portion, comprising:

a base body having a shape corresponding to a shape of the defective portion of the organ;

particles carried on the base body, the particles composed of a different material from that of the base body; and a growth-related substance contained in the organ regeneration device for growth and differentiation of cells around the defective portion.

With the organ regeneration device having the above configuration, when the organ regeneration device is placed in the defective portion of the organ, the growth-related substance contained in the organ regeneration device (the base body and/or the particles) is supplied to cells of a living body present in the defective portion of the organ and its surroundings. As a result, growth and differentiation of the cells in the defective portion are repeated so that the organ is nearly restored to its normal state.

(2) In the device described in the above-mentioned item (1), the base body has a three-dimensional network structure.

With this configuration, the base body can have a porous structure. This makes it possible for the base body to more easily and reliably carry the growth-related substance. In addition, it is also possible to allow cells present around the defective portion and cells supplied by the blood stream to easily enter the inside of the base body. This is advantageous to regeneration of an organ.

(3) In the device described in the above-mentioned item (1), the base body contains a bioabsorbable material as a major component thereof.

With this configuration, it is possible to make the base body disappear from the defective portion of the organ in the process of regeneration of the defective portion, thereby reliably preventing the base body from remaining in a living body without taking the base body out of the living body. This is advantageous to regeneration of the organ.

(4) In the device described in the above-mentioned item (3), the bioabsorbable material is soluble collagen.

With this configuration, since the soluble collagen is particularly excellent in biocompatibility, the soluble collagen is preferably used as the material constituting the base body to be placed into a living body.

(5) In the device described in the above-mentioned item (4), the base body contains a collagen sponge made of the soluble collagen as a major component thereof.

With this configuration, since the collagen sponge is bioabsorbable, it is possible to make the base body containing the collagen sponge disappear from the defective portion of the organ in the process of regeneration of the defective portion. Further, since the collagen sponge has a three-dimensional network structure, it is possible for the base body containing the collagen sponge to more easily and reliably carry the growth-related substance. As a result, the organ is more accurately regenerated.

(6) In the device described in the above-mentioned item (4), the porosity of the collagen sponge is in the range of 30 to 95%.

With this configuration, it is possible to allow cells of a living body to more easily enter the inside of the base body while maintaining the mechanical strength of the base body. As a result, the base body becomes a scaffold more suitable for tissue regeneration.

(7) In the device described in the above-mentioned item (1), at least a surface of each of the particles contains a calcium phosphate-based compound as a major component thereof.

With this configuration, since the calcium phosphate-based compound has a high affinity for various cells, such the particle is preferably used as a carrier, on the surface of which host cells can be carried.

(8) In the device described in the above-mentioned item (7), the calcium phosphate-based compound contains hydroxyapatite as a major component.

With this configuration, since hydroxyapatite is a material usable as a biomaterial, such the particle can efficiently carry host cells thereon. Further, since hydroxyapatite is much less likely to damage cells, the functions of host cells carried on the particles and cells growing and differentiating in the base body as a scaffold are not adversely affected. This makes it possible to efficiently regenerate tissue in a defective portion.

(9) In the device described in the above-mentioned item (1), the average particle size of the particles is 50 to 1000 μm.

With this configuration, it is possible to make a surface area of each of the particles sufficiently larger than the size of a host cell. Therefore, host cells can more easily adhere to the particles and grown on the surface of the particles. In addition, it is possible to make the particles to completely disappear from the defective portion of the organ in the process of regeneration of the defective portion

(10) In the device described in the above-mentioned item (1), the porosity of the particles is in the range of 10 to 75%.

This makes it possible to further increase the surface area of each of the particles, thereby further improving the adhering rate of host cells to the particles and the growth efficiency of host cells adhering to the particles. As a result, the number of host cells carried on the particle is further increased.

(11) In the device described in the above-mentioned item (1), the growth-related substance contains at least one of an angiogenesis factor and nucleic acid containing a base sequence coding for amino-acid sequence of the angiogenesis factor.

This makes it possible to promote a generation of blood vessels in the defective portion of the organ and its surroundings. Since blood vessels serve as pathways for supplying various substances required for regeneration of tissue (main organ), new blood vessels are actively formed. As a result, the substances are efficiently supplied to a field of tissue regeneration so that organ regeneration is rapidly carried out.

(12) In the device described in the above-mentioned item (11), the angiogenesis factor is at least one selected from the group comprising basic Fibroblast Growth Factor (bFGF), Vascular Endothelial Growth Factor (VEGF) and Hepatocyte Growth Factor (HGF).

With this configuration, since these angiogenesis factors are superior in blood vessel formation ability, it is possible to obtain an organ regeneration device having especially high organ regeneration ability.

(13) In the device described in the above-mentioned item (11), the growth-related substance contains at least one of a growth factor different from the angiogenesis factor and nucleic acid containing a base sequence coding for amino-acid sequence of the growth factor.

This makes it possible to promote the growth and differentiation of cells constituting appendage different from a main organ of the organ. As a result, the organ is reliably restored to its normal state.

(14) In the device described in the above-mentioned item (13), at least one of the growth factor and the nucleic acid containing a base sequence coding for amino-acid sequence of the growth factor is directly or indirectly adsorbed to the particles.

With this configuration, it is possible that the growth factor different from the angiogenesis factor released from the particles can be supplied to a proper site at proper timing. As a result, it is also possible to reliably regenerate appendage different from a main organ of the organ in its normal position.

(15) In the device described in the above-mentioned item (14), the nucleic acid is recombinant plasmid containing a base sequence derived from an expression plasmid, in which the expression plasmid is directly adsorbed to the particles.

With this configuration, it is possible to reliably produce a growth factor in cells containing the recombinant plasmid present in the defective portion of the organ and its surroundings. Therefore, it is possible to enhance the expression efficiency of the growth factor in these cells.

(16) In the device described in the above-mentioned item (15), the organ regeneration device further comprises a vector, wherein the vector is adsorbed to the particles, and the nucleic acid is introduced into the vector.

With this configuration, since the nucleic acid can be uptake into the cells through the vectors, it is possible to promote the uptake of the nucleic acid into cells due to existence of the vector. Therefore, it is possible to more rapidly regenerate tissue.

(17) In the device described in the above-mentioned item (16), the vector is derived from a non-virus.

With this configuration, it is possible to easily and reliably supply a circumscribed site with a relatively large amount of a recombinant plasmid. In addition, it is also possible to provide a higher level of safety for patients because infection does not occur.

(18) In the device described in the above-mentioned item (17), the organ regeneration device further comprises a host cell, wherein the host cell is adsorbed to the particles, and the nucleic acid is introduced into the host cell.

With this configuration, in such the organ regeneration device, a growth factor different from the angiogenesis factor is produced in the host cell. When the thus produced growth factor is secreted from the host cell, the cell whose growth and differentiation are promoted by the growth factor are selectively grown and differentiated. This makes it possible to efficiently regenerate appendage different from a main organ of the organ in a defective portion.

(19) In the device described in the above-mentioned item (1), the organ contains ectodermal tissue and endodermal tissue, and the ectodermal tissue and the endodermal tissue are present in contact with each other.

The organ regeneration device of the present invention can be preferably used for regenerating such organ.

(20) In the device described in the above-mentioned item (1), the organ is skin.

In particular, the organ regeneration device of the present invention can be preferably used for regenerating skin.

(21) In the device described in the above-mentioned item (19), the growth factor is at least one of Wingless int 3 (Wnt) and bone morphogenetic protein (BMP).

With this configuration, in the case where the organ regeneration device according to the present invention is placed into a defective portion of skin, it is also possible to form pilosebaceous units spaced at normal intervals and inclined at a normal angle.

According to the present invention, it is possible to regenerate a defective portion of an organ to restore the organ to its normal state.

For example, in the case where the organ regeneration device according to the present invention is placed into a defective portion of skin, it is possible to restore the skin to its normal state with the formation of pilosebaceous units including sebaceous glands, hair shafts, apocrine glands, etc in the defective portion. In addition, it is also possible to form pilosebaceous units spaced at normal intervals and inclined at a normal angle.

BEST MODE FOR CARRYING OUT THE INVENTION

Hereinbelow, an organ regeneration device according to the present invention will be described in detail.

Figure 1:
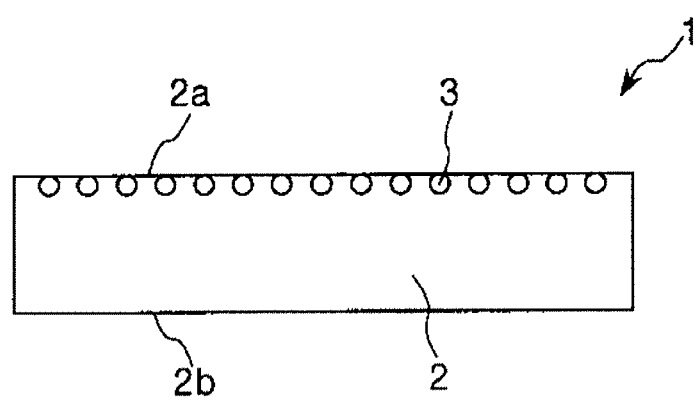
FIG. 1 is a schematic diagram showing one example of an organ regeneration device according to the present invention.

FIG. 1 is a schematic diagram showing one example of the organ regeneration device according to the present invention.

An organ regeneration device 1 according to the present invention includes a base body 2, particles 3 carried on the base body 2, and a growth-related substance (not shown) carried on at least either of the base body 2 and the particles 3. Such an organ regeneration device 1 is adapted to be used by placing it into a defective portion of an organ to regenerate the organ.

The organ regeneration device 1 can be used for regeneration of various organs, but is preferably used for regeneration of an organ (living tissue) in which ectodermal tissue and endodermal tissue are present in contact with each other.

More specifically, the organ regeneration device 1 is preferably used for regeneration of skin, peritoneum, intestinal tract, lung, kidney, liver, and secreting glands (hereinafter, collectively referred to as "organs"). Hereinbelow, a detailed description will be made with regard to an example case where the organ regeneration device 1 according to the present invention is adapted to be used for regeneration of skin having an epithelium corresponding to ectodermal tissue and dermis corresponding to endodermal tissue.

It is to be noted that in this specification, the phrase "regeneration of an organ" means that at least one of tissue and an appendage(s) of an organ is regenerated in a defective portion of an organ by repeated growth and differentiation of cells in the defective portion so that the organ is nearly restored to its original normal state.

Further, the term "defective portion" includes not only a portion inevitably damaged (lost) by, for example, burn injury, traffic accident, or illness but also a portion artificially formed by, for example, a surgical knife or a laser knife.

The base body 2 has a shape corresponding to the shape of a defective portion of an organ. Therefore, organ regeneration using the organ regeneration device 1 is carried out by embedding (placing) the base body 2 in the defective portion of the organ.

The base body 2 has a face 2a and a face 2b opposite to the face 2a. When the base body 2 is embedded in a defective portion of the organ, the face 2a of the base body 2 is located close to the surface of the organ and the face 2b of the base body 2 is located close to the deep part of the defective portion. In the following description, the face 2a of the base body 2 is referred to as a "front face" and the face 2b of the base body 2 is referred to as a "rear face".

The base body 2 has the following functions: (I) serving as a scaffold for growing and differentiating cells in a defective portion; and (II) serving as a carrier for holding the growth-related substance (which will be described later) carried thereon and/or a growth factor released from host cells carried on the particles 3 and slowly releasing them/it.

As described above, since the base body 2 has the function (I), even when a defective portion of an organ in a living body into which the organ regeneration device 1 is to be implanted is relatively large and therefore a scaffold for growing and differentiating cells has been lost, it is possible to fill the defective portion with the base body 2 by placing it as a new scaffold into the defective portion. Therefore, cells can efficiently grow and differentiate using the base body 2 as a scaffold. As a result, tissue is regenerated in the defective portion so that the organ is restored to its normal state.

Further, since the base body 2 has the function (II), it is possible to supply the growth-related substance carried thereon or a growth factor released from host cells carried on the particles 3 to a defective portion and its surroundings in a proper concentration at proper timing. As a result, tissue is reliably regenerated in the defective portion.

The base body 2 is preferably bioabsorbable. By using the bioabsorbable base body 2, it is possible to make the base body 2 disappear from a defective portion of an organ in the process of regeneration of the defective portion, thereby reliably preventing the base body 2 from remaining in a living body without taking the base body 2 out of the living body. As a result, the organ is more accurately regenerated.

It is to be noted that the term "bioabsorbable" means that the base body 2 is gradually decomposed and absorbed by into a living body and then finally disappears.

Examples of the constituent material of the bioabsorbable base body 2 include soluble collagen, gelatin, polylactic acid, polyglycolic acid, a lactic acid/glycolic acid copolymer, polycaprolactone, carboxymethylcellulose, cellulose ester, dextrol, dextran, chitosan, hyaluronic acid, Ficoll, chondroitin sulfate, polyvinyl alcohol, polyacrylic acid, polypropylene glycol, polyethylene glycol, water-soluble polyacrylate, and water-soluble polymethacrylate. These constituent materials can be used singly or in combination of two or more of them. Among them, soluble collagen is preferably used. This is because soluble collagen is particularly excellent in biocompatibility.

Further, it is preferred that the base body 2 has a three-dimensional network structure such as a porous structure. By allowing the base body 2 to have such a three-dimensional network structure, it is possible for the base body 2 to more easily and reliably carry the growth-related substance (which will be described later) and/or host cells or the like releasing a growth factor (protein). In addition, it is also possible to allow cells present around a defective portion and cells supplied by the blood stream (hereinafter, these cells are sometimes collectively referred to as "cells of a living body") to easily enter the inside of the base body 2. This is advantageous to regeneration of an organ.

In this case, the porosity of the base body 2 is preferably in the range of about 30 to 95%, and more preferably in the range of about 55 to 90%. By setting the porosity of the base body 2 to a value within the above range, it is possible to allow the cells of a living body to more easily enter the inside of the base body 2 while maintaining the mechanical strength of the base body 2. As a result, the base body 2 becomes a scaffold more suitable for tissue regeneration.

In view of the above, it is preferred that the base body 2 which is bioabsorbable and has a three-dimensional network structure is formed from a collagen sponge mainly made of soluble collagen.

The particles 3 are retained in the base body 2 and serve as carriers for carrying at least one of the growth-related substance, a vector into which the growth-related substance has been introduced, and a host cell into which the growth-related substance has been introduced. The growth-related substance carried on the particles 3 and/or a growth factor released from host cells carried on the particles 3 are/is gradually dispersed into the base body 2. Then, the growth-related substance and the growth factor dispersed into the base body 2 are supplied to a defective portion and its surroundings in proper concentrations at proper timings due to the function (II) of the base body 2.

The distribution pattern of the particles 3 in the base body 2 is not particularly limited, and therefore the particles 3 may be dispersed throughout the base body 2 or may be localized to one part of the base body 2. As will be described later, the organ regeneration device 1 can contain, as the growth-related substances, various substances which promote the growth and differentiation of cells at different timings. Therefore, it is preferred that the growth-related substance to be carried on the particles 3 is appropriately selected and the distribution of the particles 3 in the base body 2 is appropriately controlled so that the growth-related substance released from the particles 3 can be supplied to a proper site at proper timing.

More specifically, in the case where the particles 3 retained in (carried on) the base body 2 are dispersed throughout the base body 2, the growth-related substance or the like released from the particles 3 is uniformly supplied to a defective portion and its surroundings relatively early.

On the other hand, in the case where the particles 3 are localized close to the front face 2a of the base body 2, the growth-related substance or the like released from the particles 3 is supplied to a site close to the surface of an organ at a relatively early stage, but is hardly supplied to the deep part of the organ at this stage due to loss on the way to there, or even if supplied, the timing of supply to the deep part of the organ is later than that to a site close to the surface of the organ.

In the case where the particles 3 are localized close to the rear face of the base body 2, the growth-related substance or the like released from the particles 3 is relatively early supplied to the deep part of an organ, but is hardly supplied to a site close to the surface of the organ due to loss on the way to there, or even if supplied, the timing of supply to a site close to the surface of the organ is later than that to the deep part of the organ.

Based on such tendencies as described above, by controlling the distribution of the particles 3 so that the growth-related substance or the like can be supplied to a proper site in a living body at proper timing, it is possible to reliably restore an organ to a state closer to its normal state.

According to this embodiment, the particles 3 are localized close to the front face 2a of the base body 2 and are spaced apart from each other so as not to be overlapped with each other in the thickness direction of the base body 2. This makes it possible to sufficiently provide the pathways of the growth-related substance or the like dispersed from the individual particles 3 into the base body 2 and thereby to efficiently supply the growth-related substance or the like to a site around a defective portion of an organ.

The particles 3 may stay in their original positions after the base body 2 is embedded in a defective portion of an organ or may be gradually settled from the front face 2a side to the rear face 2b side of the base body 2 (i.e., in the thickness direction of the base body 2).

In the case where the particles 3 stay in their original positions, the growth-related substance released from the particles 3 is continuously supplied to a certain region. This makes it possible to rapidly and reliably regenerate tissue whose regeneration is induced by the growth-related substance in this region.

On the other hand, In the case where the particles 3 are gradually settled from the front face 2a side to the rear face 2b side, a site to which the growth-related substance released from the particles 3 is supplied shifts from the surface side to the deep part side of an organ with time. This is advantageous to regeneration of an organ having an appendage(s) elongating in the thickness direction of the main body thereof.

It is to be noted that the degree of settling (i.e., ease of settling) of the particles 3 in the base body 2 can be controlled by regulating the mass and average particle size of the particle 3 and the average pore size and physical properties such as viscoelasticity of the base body 2.

Hereinbelow, the structure of the particle 3 will be described.

The particles 3 shown in FIG. 1 have a substantially circular shape. It is to be noted that the shape of the particle 3 is not limited to it, and the particle 3 can have any shape such as oval, needle-like, or leaf-like, but preferably has a substantially circular shape. This makes it possible to highly uniformly attach the growth-related substance to the particles 3. In addition, it is also possible to highly uniformly grow cells attached to the particles 3. Further, such particles 3 can be more uniformly suspended in, for example, a culture solution having cells suspended therein to culture the cells on the surface of the particles 3 under stirring.

The constituent material of the particle 3 is not particularly limited as long as it is biocompatible and is different from the constituent material of the base body 2. Examples of such a constituent material of the particle 3 include: calcium phosphate-based compounds such as hydroxyapatite, fluorine apatite, carbonate apatite, dicalcium phosphate, tricalcium phosphate, tetracalcium phosphate, and octacalcium phosphate; ceramic materials such as alumina, titania, zirconia, and yttria; and various metal materials such as titanium or titanium alloys, stainless steel, Co—Cr-based alloys, and Ni—Ti-based alloys. These materials can be used singly or in combination of two or more of them.

In this embodiment, it is preferred that at least the surface of the particle 3 and its vicinity are mainly made of a calcium phosphate-based compound. This is because since a calcium phosphate-based compound has a high affinity for various cells (cell affinity), such a particle 3 is preferably used as a carrier, on the surface of which host cells can be carried.

According to this embodiment, the entire of the particle 3 is mainly made of a calcium phosphate-based compound. This is because since a calcium phosphate-based compound is bioabsorbable, the particles 3, the entire of which is made of a calcium phosphate-based compound have excellent bioabsorbability and therefore disappear from a defective portion after the defective portion is healed. This makes it possible to prevent foreign matter derived from the particles from remaining in the healed portion and thereby to restore an organ to a state closer to its normal state. Further, the particle 3, the entire of which is made of a calcium phosphate-based compound can efficiently carry the growth-related substance or host cells thereon.

The calcium phosphate-based compound is not particularly limited as long as its Ca/P ratio is in the range of 1.0 to 2.0. Examples of such a calcium phosphate-based compound include $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca(PO_3)_2$, and $CaHPO_4$. These compounds can be used singly or in combination of two or more of them.

In this embodiment, it is preferred that the particle 3 is mainly made of hydroxyapatite ($Ca_{10}(PO_4)_6(OH)_2$). This is because since hydroxyapatite is a material usable as a biomaterial, such a particle 3 can efficiently carry host cells thereon. Further, since hydroxyapatite is much less likely to damage cells, the functions of host cells carried on the particles and cells growing and differentiating in the base body as a scaffold are not adversely affected. This makes it possible to efficiently regenerate tissue in a defective portion.

It is to be noted that these calcium phosphate-based compounds can be synthesized by a well-known wet or dry synthesis method. A calcium phosphate-based compound synthesized by such a method may contain a material remaining after synthesis (e.g., a raw material) or a secondary reaction product or the like produced during synthesis.

In the case where the particle 3 is made of a calcium phosphate-based compound, as described above, it is preferred that the surface of the particle 3 and its vicinity are mainly made of a calcium phosphate-based compound. In this case, the inner part of the particle 3 may be formed from a substrate mainly made of a resin material. By allowing the particle 3 to have such a structure, it is possible to relatively easily control the shape, size (e.g., average particle size), and physical properties (e.g., density) of the particle 3.

Examples of the resin material constituting the base include various thermosetting resins and various thermoplastic resins. Specific examples of the thermoplastic resin materials include polyamides (e.g., nylon 6, nylon 66, nylon 6-10, nylon 12), polyethylene, polypropylene, polystyrene, polyimide, acrylic resins, and thermoplastic polyurethanes. Specific examples of the thermosetting resin materials include epoxy resins, phenol resins, melamine resins, urea resins, unsaturated polyesters, alkyd resins, thermosetting polyurethanes, and ebonite. These resins can be used singly or in combination of two or more of them. In this embodiment, it is preferred that the resin material constituting the base mainly contains at least one of polyamide resin and epoxy resin. This is because, for example, in the case where the base is covered with fine covering particles mainly made of a calcium phosphate-based compound, these fine covering particles are provided on the base so that a part of the covering particle is embedded into the surface of the base and its vicinity. As a result, the base made of the above-mentioned resin material can have an appropriate hardness. This makes it possible to easily and reliably cover the base with the covering particle.

The size of the particle 3 is not particularly limited. However, when the maximum length of cells (cells allowed to adhere to the particles 3) is defined as L1 (μm) and the average particle size of the particles 3 is defined as L2 (μm), L2/L1 is preferably in the range of 2 to 100, and more preferably in the range of 5 to 50. More specifically, L2 is preferably in the range of about 50 to 1000 μm, and more preferably in the range of about 50 to 500 μm, and more even preferably in the range of about 70 to 250 μm.

By allowing the particle 3 to have an average particle size within the above range, it is possible to make its surface area sufficiently larger than the size of a cell. Therefore, cells can more easily adhere to the particles 3 and grown on the surfaces of the particles 3. It is to be noted that if the average particle size of the particles 3 is too small, there is a case where cells cannot efficiently adhere to the particles 3. In addition, there is also a case where the particles 3 easily agglomerate together. On the other hand, if the average particle size of the particles 3 is too large, it is difficult to make the particles 3 to completely disappear from a living body after a defective portion is healed, and therefore there is a possibility that foreign matter derived from the particles 3 will remain in a regenerated organ in the living body. Further, when the average particle size of the particles 3 is large, the settling velocity of the particles 3 in a culture solution becomes large, and therefore it is necessary to increase the agitating speed of the culture solution during cell culture (see the description below). In this case, there is a fear that the particles 3 come into collision with each other so that host cells adhering to the surfaces of the particles 3 will be damaged.

From the viewpoint of more uniformly suspending the particles 3 in a culture solution, the density of the particle 3 is preferably close to that of water. More specifically, the density of the particle 3 is preferably in the range of about 0.8 to 1.4 $g/cm^3$, and more preferably in the range of about 0.9 to 1.2 $g/cm^3$. By setting the density of the particle 3 to a value within the above range, it is possible to more uniformly suspend the particles 3 in a culture solution.

Further, it is also preferred that at least the surface of the particle 3 and its vicinity are porous. This makes it possible to further increase the surface area of the particle 3, thereby further improving the adhering rate of host cells to the particle 3 and the growth efficiency of host cells adhering to the particle 3. As a result, the number of host cells carried on the particle 3 is further increased.

More specifically, the porosity of the particle 3 is preferably in the range of about 10 to 75%, and more preferably in the range of about 30 to 60%. By setting the porosity of the particle 3 to a value within the above range, the above-described effects are more remarkably exhibited.

The growth-related substance is a substance having the function of directly or indirectly promoting the growth and differentiation of cells. Such a growth-related substance is directly or indirectly carried on at least either of the base body 2 and the particles 3.

The term "substance directly promoting the growth and differentiation of cells" used in this specification refers to a substance promoting the growth and differentiation of cells through contact with the cells, that is, a growth factor (protein).

The term "substance indirectly promoting the growth and differentiation of cells" refers to a substance involved in the production (synthesis) of a growth factor when introduced into a cell. A specific example of such a substance includes a nucleic acid containing a base sequence coding for the amino acid sequence of a growth factor (hereinafter, also referred to as a "growth-related nucleic acid"). When such a growth-related nucleic acid is introduced into a host cell, the cell successively produces a growth factor using a base sequence coding for the amino acid sequence of the growth factor as a template. The thus produced growth factor promotes the growth and differentiation of cells present in a defective portion and its surroundings.

Here, the growth-related nucleic acid may be used in such a manner that it is introduced into the cells of a living body having been present in a defective portion and its surroundings and then expressed inside or outside the organ regeneration device 1 so that a growth factor is produced. Alternatively, the growth-related nucleic acid may also be used in such a manner that host cells having the growth-related nucleic acid introduced thereinto are carried on at least either of the base body 2 and the particles 3 of the organ regeneration device 1 so that a growth factor is released from the host cells. This will be described later in detail.

Among these growth-related substances, when a growth factor (protein) is used, the growth and differentiation of cells are directly promoted. This makes it possible to relatively early regenerate tissue and/or an appendage(s) of an organ whose regeneration is induced by the growth factor. Further, the use of a growth factor as the growth-related substance is advantageous in that the amount of a growth factor to be supplied to a site around a defective portion can be easily controlled.

On the other hand, when a nucleic acid containing a base sequence coding for the amino acid sequence of a growth factor (a growth-related nucleic acid) is used as the growth-related substance, a growth factor can be produced relatively late as compared to a case where a growth factor (protein) is used as the growth-related substance, and can be continuously supplied (slow-released) to a defective portion and its surroundings. Further, even when the growth factor is relatively more likely to be denatured, the growth factor can be supplied in a non-denatured state to a defective portion and its surroundings for a long period of time. Therefore, the use of such a nucleic acid as the growth-related substance makes it possible, even when a defective portion is relatively large, to reliably regenerate tissue and/or an appendage(s) of an organ whose regeneration is induced by a growth factor corresponding to the nucleic acid.

Examples of such a growth factor include, but are not limited to: morphogens such as DPP (decapentaplegic), transforming growth factor β, Hh (Hedgehog), shh (sonic Hedgehog), Wingless int 3 (Wnt), bone morphogenic protein (BMP), Epidermal growth factor, and insulin-like growth factor (ILGF); and angiogenesis factors such as basic Fibroblast Growth Factor (bFGF), Vascular Endothelial Growth Factor (VEGF), Hepatocyte Growth Factor (HGF), Granulocyte Macrophage-Colony Stimulating Factor (GM-CSF), Granulocyte-Colony Stimulating Factor (G-CSF), Macrophage-Colony Stimulating Factor (M-CSF), Stem Cell Factor (SCF), Angiopoietin-1, Angiopoietin-2, ribonuclease-like protein, nicotinamide, prostaglandin E (prostaglandin E1, prostaglandin E2, prostaglandin E3), proline derivatives, and cyclic AMP derivatives such as dibutyl cyclic AMP (dBc AMP). These growth factors can be used singly or in combination of two or more of them.

Among these growth factors, angiogenesis factors are growth factors capable of promoting the formation of blood vessels. Among the above-mentioned angiogenesis factors, at least one of basic Fibroblast Growth Factor (bFGF), Vascular Endothelial Growth Factor (VEGF), and Hepatocyte Growth Factor (HGF) is particularly preferred. This is because these angiogenesis factors are superior in blood vessel formation ability, thereby making it possible to obtain an organ regeneration device 1 having especially high organ regeneration ability.

On the other hand, morphogens are growth factors capable of promoting the growth and differentiation of cells (cells constituting an appendage(s) of an organ) governing the properties (characteristics) of an organ or tissue to be regenerated. Therefore, in the case where the organ regeneration device 1 is used for regeneration of skin as described with reference to this embodiment, at least one of Wnt and BMP believed to be involved in the regeneration of pilosebaceous units of skin is preferably used as a morphogen.

BMP is not particularly limited as long as it has activity that promotes the regeneration of pilosebaceous units. Examples of such BMP include BMP1, BMP2, BMP3, BMP4, BMP5, BMP6, BMP7, BMP8, BMP9, BMP12 (homodimers), heterodimers thereof, and modified versions thereof (i.e., proteins each having an amino acid sequence obtained by subjecting the amino acid sequence of naturally-occurring BMP to deletion, substitution, and/or addition of one or more amino acids, while maintaining the same activity as the naturally-occurring BMP).

Similarly, Wnt is not particularly limited as long as it has the activity that promotes the regeneration of pilosebaceous units. Examples of such Wnt include Wnt, SHH, BMP Notch signal, Friizzied, Nestin, and Hairless.

Unlike the case described with reference to this embodiment, when the organ regeneration device 1 is used for regeneration of lung, bFGF is preferably used as a morphogen, and when the organ regeneration device 1 is used for regeneration of kidney, at least one of Wnt and HGF is preferably used as a morphogen, and when the organ regeneration device 1 is used for regeneration of liver, HGF is preferably used as a morphogen.

Such a growth factor as described above may be carried on both the base body 2 and the particles 3, or may be carried on either of them. It is preferred that the carrier of a growth factor is appropriately selected according to the kind(s) or distribution of tissue and/or an appendage(s) of an organ whose regeneration is induced by the growth factor.

For example, a growth factor carried on the base body 2 is uniformly supplied to a defective portion and its surroundings relatively early.

On the other hand, in the case where a growth factor is carried on the particles 3, a site in a living body to which the growth factor is to be supplied and the timing of supply of the growth factor can be controlled by regulating the distribution and/or the degree of settling of the particles 3 in the base body 2.

Therefore, a growth factor involved in the regeneration of tissue as the main body of an organ (main organ) such as skin tissue, that is, an angiogenesis factor is preferably carried on the base body 2.

On the other hand, a growth factor involved in the regeneration of an appendage(s) locally existing in a main organ (e.g., in the case of skin, pilosebaceous units), that is, a morphogen (a growth factor other than angiogenesis factors) is preferably carried on the particles 3.

By using the organ regeneration device 1 having such a structure, tissue as the main body of an organ is early regenerated, and then an appendage(s) (pilosebaceous units) is(are) reliably regenerated in its(their) normal position using the tissue as a foundation.

In the case where a growth factor is carried on the base body 2, the amount of the growth factor to be used is not particularly limited, but is preferably in the range of about 1 to 100 μg, and more preferably in the range of about 10 to 70 μg per $cm^3$ of the base body 2.

Similarly, also in the case where a growth factor is carried on the particles 3, the amount of the growth factor to be used is not particularly limited, but is preferably in the range of about 1 to 100 μg, and more preferably in the range of about 10 to 70 μg per $cm^3$ of the particles 3.

In either case as described above, if the amount of a growth factor to be used is too small, there is a case where tissue regeneration is not rapidly promoted. On the other hand, even if the amount of a growth factor to be used exceeds the above upper limit value, an effect obtained by using a growth factor is not enhanced in proportion to the amount thereof.

The base body 2 carrying a growth factor can be formed (produced) by bringing a growth factor into contact with the base body 2. More specifically, the base body 2 carrying a growth factor can be easily formed by, for example, supplying a liquid (a solution or a suspension) containing a growth factor to the base body 2 or immersing the base body 2 in such a liquid.

The particles 3 carrying a growth factor can be formed (produced) by bringing a growth factor into contact with the particles 3. More specifically, the particles 3 carrying a growth factor can be easily produced by, for example, supplying a liquid (a solution or a suspension) containing a growth factor to the particles 3 or immersing the particles 3 in such a liquid.

A growth-related nucleic acid is a nucleic acid containing a base sequence coding for the amino acid sequence of a growth factor as described above. As the base sequence of such a nucleic acid, cDNA is usually used.

The base sequence is not particularly limited as long as it is the same as that coding for a naturally-occurring growth factor or it is a base sequence obtained by subjecting a base sequence coding for a naturally-occurring growth factor to deletion, substitution, and/or addition of one or more bases. These base sequences can be used singly or in combination of two or more of them.

Meanwhile, a growth-related nucleic acid is taken up by cells (host cells carried on the organ regeneration device 1 (which will be described later) or the cells of a living body present in a defective portion of an organ and its surroundings), and then a growth factor is produced in these cells using the growth-related nucleic acid as a template. In this case, unlike a case where a growth factor is directly introduced into the organ regeneration device 1, a growth factor derived from the growth-related nucleic acid is produced late in the organic regeneration device 1.

In the case where the organ regeneration device 1 is used for regeneration of skin as described with reference to this embodiment, at least one of Wnt and BMP is preferably used as a morphogen as described above. Since such morphogens are involved in the regeneration of pilosebaceous units, they are preferably produced after main organs such as blood vessels and epidermis are formed in skin. For this reason, it is preferred that a growth factor such as an angiogenesis factor is directly contained in the organ regeneration device 1 in the form of a growth factor (protein). On the other hand, a growth factor such as Wnt or BMP (a growth factor other than angiogenesis factors) is preferably produced from a nucleic acid (a growth-related nucleic acid) containing a base sequence coding for the amino acid sequence of the growth factor.

A nucleic acid (cDNA) containing a base sequence coding for the amino acid sequence of BMP can be obtained by a method described in, for example, Translated National Publications of Patent Applications Nos. H2-500241, H3-503649, and H3-505098.

A nucleic acid (cDNA) containing a base sequence coding for the amino acid sequence of Wnt can be obtained by a method described in, for example, Kobune M et at: Wnt3/RhoA/ROCK signaling pathway is involved in adhesion-mediated drug resistance of multiple myeloma in an autocrine mechanism. Mol Cancer Ther 6: 1774-1784, 2007.

Such a growth-related nucleic acid is not particularly limited as long as it contains a base sequence coding for the amino acid sequence of a growth factor, but one containing a base sequence derived from an expression plasmid, that is, one obtained by splicing (introducing) a base sequence coding for the amino acid sequence of a growth factor into an expression plasmid is preferably used. It is to be noted that in the following description, a growth-related nucleic acid obtained by splicing a base sequence coding for the amino acid sequence of a growth factor into an expression plasmid is also referred to as a "recombinant plasmid".

By using such a recombinant plasmid, it is possible to reliably produce (express) a growth factor in cells (host cells carried on the organ regeneration device 1 (which will be described alter) or the cells of a living body present in a defective portion of an organ and its surroundings) which have taken up the recombinant plasmid, thereby significantly enhancing the expression efficiency of the growth factor in these cells.

An expression plasmid to be used can be selected from various plasmids widely used in the field of genetic engineering. Examples of such an expression plasmid include pCAH, pCAcc, pSC101, pBR322, and pUC18, and these expression plasmids can be used singly or in combination of two or more of them.

If necessary, a base sequence (a DNA fragment) for properly controlling the expression of a growth factor may be introduced into the recombinant plasmid.

A base sequence coding for the amino acid sequence of a growth factor and other base sequences can be spliced into an expression plasmid by a well-known method.

Figure 2:
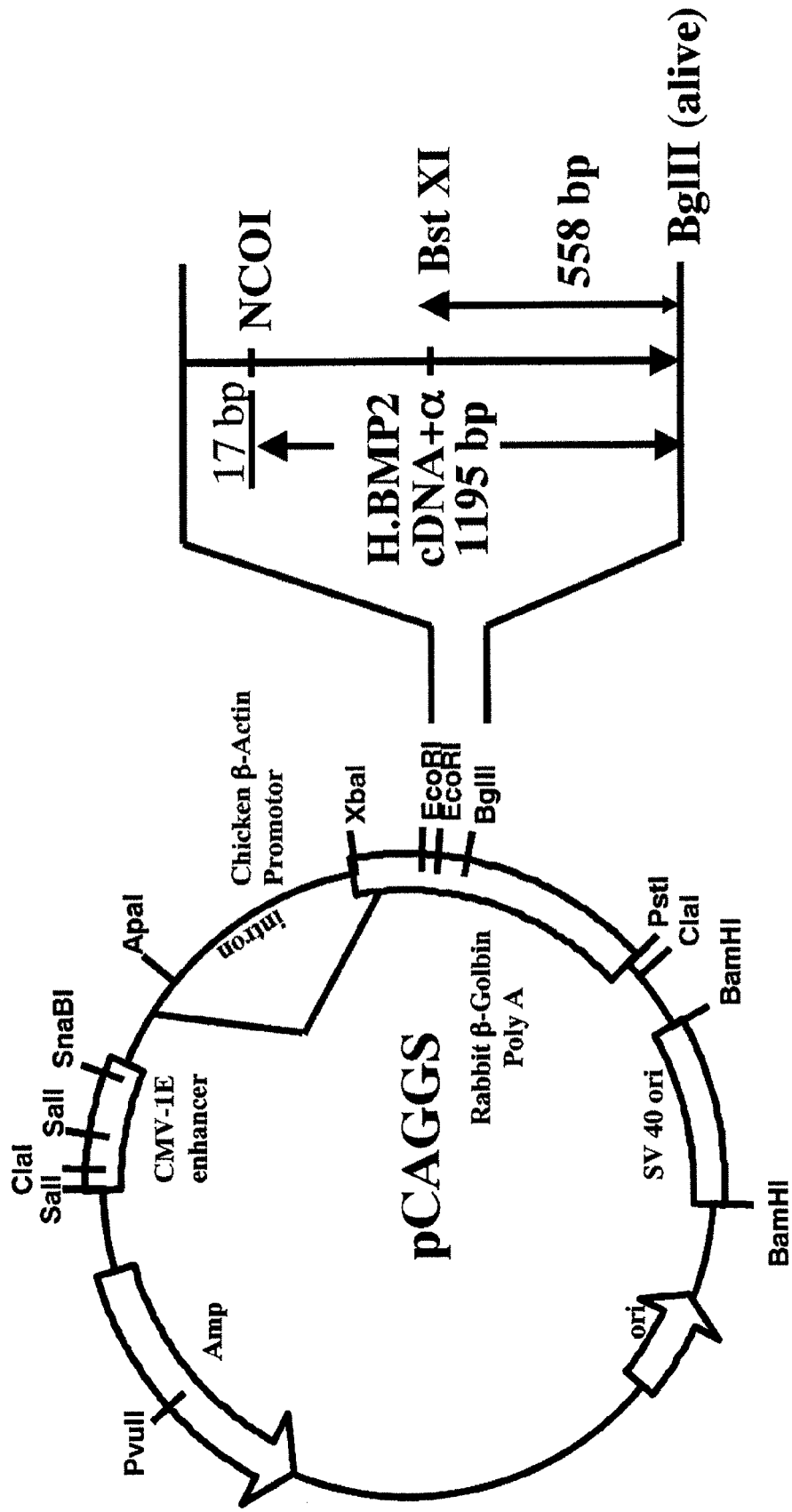
FIG. 2 shows a recombinant plasmid obtained by splicing cDNA coding for the amino acid sequence of BMP 2 into an expression plasmid, pCAH.

FIG. 2 shows, as one example of the recombinant plasmid, a recombinant plasmid obtained by introducing cDNA coding for the amino acid sequence of BMP 2 into an expression plasmid, pCAH.

This recombinant plasmid contains a DNA fragment resistant to Amp (ampicillin). In addition, a DNA fragment containing an enhancer-promoter derived from cytomegalovirus (CMV) and a DNA fragment containing a transcription termination signal derived from SV40 are spliced into the recombinant plasmid. The DNA fragment containing a transcription termination signal derived from SV40 is located downstream from the BMP2 cDNA.

Figure 3:
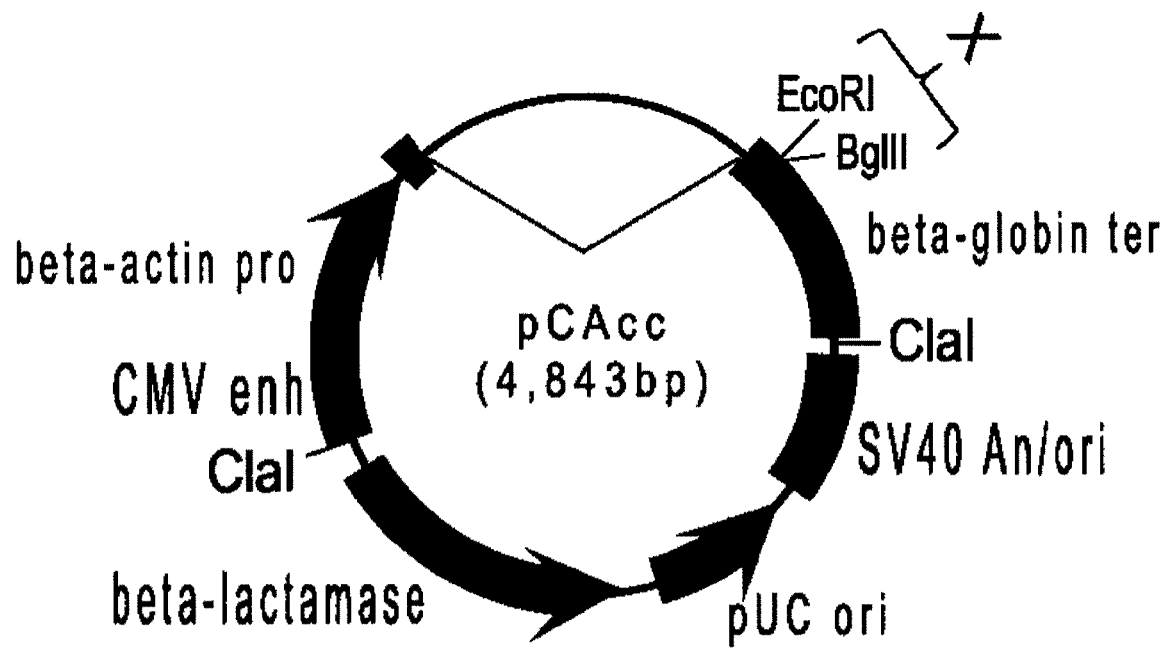
FIG. 3 shows a recombinant plasmid obtained by splicing cDNA coding for the amino acid sequence of Wnt into an expression plasmid, pCAcc.

Further, FIG. 3 shows, as another example of the recombinant plasmid, a recombinant plasmid obtained by introducing cDNA coding for the amino acid sequence of Wnt into a region represented by X of an expression plasmid, pCAcc.

This recombinant plasmid contains a DNA fragment resistant to a β-lactamase inhibitor. In addition, a DNA fragment containing an enhancer-promoter derived from cytomegalovirus (CMV) and a DNA fragment containing a transcription termination signal derived from SV40 are spliced into the recombinant plasmid. The DNA fragment containing a transcription termination signal derived from SV40 is located downstream from the Wnt cDNA.

As is the case with the above-described growth factor, such a growth-related nucleic acid may be carried on both the base body 2 and the particles 3 or may be carried on either of them.

Further, such a growth-related nucleic acid may be directly carried on the base body 2 and/or the particles 3 in the form of a recombinant plasmid or may be indirectly carried on the base body 2 and/or the particles 3 by introducing it into a vector or a host cell which will be described later.

In the case where the organ regeneration device 1 containing a growth-related nucleic acid carried on the base body 2 and/or the particles 3 in the form of a recombinant plasmid is embedded in a defective portion, the growth-related nucleic acid is introduced into the cells of a living body transferred into the organ regeneration device 1 from the defective portion and it surroundings, or the growth-related nucleic acid itself is released from the organ regeneration device 1 and then introduced into the cells of a living body present in the defective portion and its surroundings.

When a growth-related nucleic acid carried on the base body 2 and/or the particles 3 in the form of a recombinant plasmid is introduced into cells in such a manner as described above, a growth factor is produced in these cells. When the thus produced growth factor is secreted outside the cells, cells whose growth and differentiation are promoted by the growth factor are selectively grown and differentiated.

It is preferred that a carrier for carrying a growth-related nucleic acid (a recombinant plasmid) is appropriately selected according to the kinds or distribution of tissue and an appendage(s) of an organ whose regeneration is indirectly induced by the growth-related nucleic acid.

For example, a growth-related nucleic acid carried on the base body 2 is uniformly supplied to a defective portion and its surroundings relatively early.

On the other hand, in the case where a growth-related nucleic acid is carried on the particles 3, a site in a living body to which the growth-related nucleic acid is to be supplied and the timing of supply of the growth-related nucleic acid can be controlled by regulating the distribution or the degree of settling of the particles 3 in the base body 2.

Therefore, a growth-related nucleic acid involved in the regeneration of tissue as the main body of an organ (main organ) such as skin tissue (a nucleic acid containing a base sequence coding for the amino acid sequence of an angiogenesis factor) is preferably carried on the base body 2.

On the other hand, a growth-related nucleic acid involved in the regeneration of an appendage(s) locally existing in a main organ (e.g., in the case of skin, pilosebaceous units) (a nucleic acid containing a base sequence coding for the amino acid sequences of, for example, BMP and Wnt) is preferably carried on the particles 3.

By using the organ regeneration device 1 having such a structure, tissue as the main body of an organ is early regenerated and then an appendage(s) (pilosebaceous units) is(are) reliably regenerated in its(their) normal position using the tissue as a foundation.

The base body 2 carrying a growth-related nucleic acid (a recombinant plasmid) can be formed (produced) by bringing a growth-related nucleic acid into contact with the base body 2. More specifically, the base body 2 carrying a growth-related nucleic acid can be easily formed by, for example, supplying a liquid (a solution or a suspension) containing a growth-related nucleic acid to the base body 2 or immersing the base body 2 in such a liquid.

The particles 3 carrying a growth-related nucleic acid (a recombinant plasmid) can be formed (produced) by bringing a growth-related nucleic acid into contact with the particles 3. More specifically, the particles 3 carrying a growth-related nucleic acid can be easily formed by, for example, supplying a liquid (a solution or a suspension) containing a growth-related nucleic acid to the particles 3 or immersing the particles 3 in such a liquid.

In order to improve the efficiency of introduction (uptake) of a recombinant plasmid (a growth-related nucleic acid) into the cells of a living body, that is, in order to allow a larger amount of a growth factor to be secreted in the cells of a living body earlier, it is preferred that the recombinant plasmid (growth-related nucleic acid) is indirectly carried on the base body 2 and/or the particles 3 by introducing it into a vector.

It is to be noted that the term "vector" refers to one having the function of holding a recombinant plasmid and promoting the uptake of the recombinant plasmid into cells present around a defective portion. The use of such a vector makes it possible to more rapidly regenerate tissue.

In the present invention, as such a vector, either a vector which is not derived from a virus (i.e., a non-viral vector) or a virus-derived vector such as an adenovirus vector or a retrovirus vector may be used. Among these vectors, a non-viral vector is particularly preferably used. By using a non-viral vector, it is possible to easily and reliably supply a circumscribed site with a relatively large amount of a recombinant plasmid. In addition, it is also possible to provide a higher level of safety for patients because infection does not occur. Further, a method using a non-viral vector is excellent in that it is possible to save time and effort. This is because an ex vivo method using a virus vector or a cell requires, for example, the operation to introduce a nucleic acid into a virus vector or a cell and the operation to grow the virus vector or the cell into which the nucleic acid has been introduced, but a method using a non-viral vector does not require such operations.

As a non-viral vector, a liposome (a lipid membrane) is preferably used among various non-viral vectors. This is because a liposome is made of a component similar to that of a cell membrane so that the liposome is relatively easily and smoothly bound to (fused with) the cell membrane. This makes it possible to further improve the efficiency of uptake of a growth-related nucleic acid into cells.

As a liposome, for example, a cationic liposome capable of adsorbing a recombinant plasmid to the surface thereof or an anionic liposome capable of internally incorporating a recombinant plasmid can be used. These liposomes can be used singly or in combination of two or more of them.

A cationic liposome is mainly made of polycationic lipid such as DOSPA (2,3-dioleyloxy-N-[2(sperminecarboxamido)ethyl]-N,N-dimethyl-1-propanaminium trifluoroacetate). As such a cationic liposome, for example, "SuperFect" (manufactured by QIAGEN) commercially available can be used.

On the other hand, an anionic liposome is mainly made of phospholipid such as 3-sn-phosphatidylcholine, 3-sn-phosphatidylserine, 3-sn-phosphatidyl ethanolamine, 3-sn-phosphatidal ethanolamine, or derivatives thereof.

The amount of a vector to be used is not particularly limited, but the mixing ratio between a vector and a recombinant plasmid is preferably in the range of about 1:1 to 20:1 by weight, and more preferably in the range of about 2:1 to 10:1 by weight. If the amount of a vector to be used is too small, there is a case where it is impossible to sufficiently improve the efficiency of uptake of the recombinant plasmid into cells depending on, for example, the kind of vector used. On the other hand, even if a vector is used in an amount exceeding the above upper limit value, an effect obtained by using a vector is not enhanced in proportion to the amount thereof. In addition, the use of such an excessive amount of a vector increases production costs and has a possibility that cytotoxity develops, which is disadvantageous for organ regeneration.

The base body 2 carrying a vector into which a recombinant plasmid has been introduced can be formed (produced) by bringing the recombinant plasmid and the vector into contact with the base body 2. More specifically, the base body 2 carrying a vector into which a recombinant plasmid has been introduced can be easily formed by, for example, supplying a liquid containing both the recombinant plasmid and the vector to the base body 2 or immersing the base body 2 in such a liquid.

The particles 3 carrying a vector into which a recombinant plasmid has been introduced can be formed (produced) by bringing the recombinant plasmid and the vector into contact with the particles 3. More specifically, the particles 3 carrying a vector into which a recombinant plasmid has been introduced can be easily formed by, for example, supplying a liquid containing both the recombinant plasmid and the vector to the particles 3 or immersing the particles 3 in such a liquid.

In the case of using the organ regeneration device 1 in which a growth-related nucleic acid (a recombinant plasmid) is indirectly carried on the base body 2 and/or the particles 3 by introducing it into host cells, a growth factor is produced in these host cells. When the thus produced growth factor is secreted (released) from the host cells, cells whose growth and differentiation are promoted by this growth factor are selectively grown and differentiated. By selecting a host cell excellent in the efficiency of introduction of a growth-related nucleic acid and the ability to produce a growth factor for use in the organ regeneration device 1 having such a structure as described above, it is possible to efficiently supply a growth factor to the cells of a living body present around a defective portion and thereby to rapidly regenerate an organ.

A host cell into which a growth-related nucleic acid is to be introduced is not particularly limited, and various cells can be used. Examples of such a host cell include blast cells such as a fibroblast (a skin fibroblast), an odontoblast, and an osteoblast. These host cells can be used singly or in combination of two or more of them. Among them, a fibroblast is preferably used as a host cell. This is because since a fibroblast is easy to grow but is difficult to differentiate, the organ regeneration device 1 using a fibroblast as a host cell can stably supply a sufficient amount of a growth factor. In addition, it is also possible to reliably prevent organ regeneration from being adversely affected by differentiation of the host cells contained in the organ regeneration device 1.

It is preferred that a carrier for carrying host cells into which a growth-related nucleic acid has been introduced is appropriately selected according to the kinds or distribution of tissue and an appendage(s) of an organ whose regeneration is indirectly induced by the growth-related nucleic acid.

For example, a growth factor released from host cells carried on the base body 2 is uniformly supplied to a defective portion and its surroundings relatively early.

On the other hand, in the case where host cells are carried on the particles 3, a site in a living body to which a growth factor released from the host cells is to be supplied and the timing of supply of the growth factor can be controlled by regulating the distribution or the degree of settling of the particles 3 in the base body 2.

Therefore, for example, host cells into which a growth-related nucleic acid involved in the regeneration of tissue as the main body of an organ, such as skin tissue, has been introduced are preferably carried on the base body 2. On the other hand, host cells into which a growth-related nucleic acid (more specifically, a nucleic acid coding for, for example, BMP and Wnt) involved in the regeneration of an appendage (s) locally existing in a main organ (e.g., in the case of skin, pilosebaceous units) has been introduced are preferably carried on the particles 3. This makes it possible to early construct tissue as the main body of an organ. In addition, it is also possible to reliably regenerate an appendage(s) of the organ in its (their) normal position using the tissue as a foundation.

It is to be noted that when the particles 3, at least the surface and its vicinity of which are mainly made of a calcium phosphate-based compound, as described above are used as carriers of host cells, the host cells can efficiently adhere to the surfaces of the particles 3 and grown because the particles 3 have a high affinity for the host cells.

Such particles 3 carrying host cells into which a growth-related nucleic acid (a recombinant plasmid) has been introduced can be obtained, for example, through the following steps.

<A1> First, a culture solution in which the particles and host cells allowed to adhere to the particles 3 are suspended is prepared.

The culture solution is not particularly limited and is appropriately selected according to, for example, the kind of host cells to be used. Examples of such a culture solution include MEM medium, α MEM medium, Dulbecco's MEM medium, BME medium, MCDB-104 medium, and MSCB medium.

If necessary, such a culture solution may contain additives such as blood serum, serum protein (e.g., albumin), various vitamins, various amino acids, and salts.

Then, the culture solution prepared is agitated. By doing so, it is possible to allow the host cells to substantially uniformly adhere the host cells to the surface of the particles 3 so that the host cells are grown on the surfaces of the particles 3 with a lapse of time. In addition, it is also possible to bring the culture solution into contact with the host cells substantially uniformly, thereby improving the efficiency of growth of the host cells.

The agitation speed of the culture solution is not particularly limited, but is preferably in the range of about 5 to 100 rpm, and more preferably in the range of about 10 to 50 rpm. If the agitation speed is too low, there is a case where it is impossible to uniformly disperse the particles 3 in the culture solution depending on the density, average particle size, etc of the particles 3. In this case, there is a fear that the host cells cannot be sufficiently grown on the surfaces of the particles 3. On the other hand, if the agitation speed is too high, there is a fear that the particles 3 are excessively agitated and vigorously come into collision with each other so that the host cells adhering to the particles 3 are damaged.

Further, the temperature (incubation temperature) of the culture solution is not particularly limited and is appropriately set according to the kind of host cells to be cultured. However, the temperature of the culture solution is usually in the range of about 20 to 40° C., preferably in the range of about 25 to 37° C.

<A2> Then, after the completion of the step <A1>, the culture solution in which the particles 3 are suspended is mixed with a suspension of a growth-related nucleic acid (e.g., a recombinant plasmid), and the thus obtained mixture is left standing. By doing so, it is possible to introduce the growth-related nucleic acid into the host cells which have been grown on the surfaces of the particles 3.

It is to be noted that the growth-related nucleic acid is preferably held by a vector. This makes it possible to promote the uptake of the growth-related nucleic acid into the host cells.

As the vector, for example, the same one as described above can be used.

The temperature (treatment temperature) of the culture solution is not particularly limited, but is usually in the range of about 20 to 40° C., preferably in the range of about 25 to 37° C.

Further, the time for treatment is not particularly limited, but is usually in the range of about 0.1 to 5 hours, preferably in the range of about 1 to 3 hours.

The base body 2 carrying host cells into which a growth-related nucleic acid (a recombinant plasmid) has been introduced can be obtained, for example, through the following steps.

<B1> First, a culture solution in which host cells allowed to adhere to the base body 2 are suspended is prepared.

Examples of the culture solution include the same ones as described above.

Then, the base body 2 is immersed in the culture solution prepared. By doing so, it is possible to attach the host cells to the surface of the base body 2 so that the host cells are grown with a lapse of time.

The temperature (incubation temperature) of the culture solution is not particularly limited, and is appropriately set according to the kind of host cells to be cultured. However, the temperature of the culture solution is usually in the range of about 20 to 40° C., preferably in the range of about 25 to 37° C.

<B2> Then, after the completion of the step <B1>, the culture solution in which the base body 2 is immersed is mixed with a suspension of a growth-related nucleic acid (e.g., a recombinant plasmid), and the thus obtained mixture is left standing. By doing so, it is possible to introduce the growth-related nucleic acid into the host cells which have been grown on the surfaces of the base body 2.

It is to be noted that the growth-related nucleic acid is preferably held by a vector. This makes it possible to promote the uptake of the growth-related nucleic acid into the host cells. As such a vector, for example, the same one as described above can be used.

The temperature (treatment temperature) of the culture solution is not particularly limited, but is usually in the range of about 20 to 40° C., preferably in the range of about 25 to 37° C.

The time for treatment is not particularly limited, but is usually in the range of about 0.1 to 5 hours, preferably in the range of about 1 to 3 hours.

The above-described growth factor, growth-related nucleic acid (a recombinant plasmid), vector into which a growth-related nucleic acid has been introduced, and host cell into which a growth-related nucleic acid has been introduced can be used singly or in combination of two or more of them. However, in a the case where the organ regeneration device 1 is intended to regenerate an organ using two or more growth-related substances which preferably act on cells at different timings, two or more of them are preferably used in combination.

More specifically, in the case of using the organ regeneration device 1 carrying a growth factor (protein), the growth factor directly promotes the growth and differentiation of cells. Therefore, it is possible to allow the growth factor to relatively early act on cells in a living body.

In the case of using the organ regeneration device 1 carrying host cells into which a growth-related nucleic acid has been introduced, a growth factor is produced in these host cells and is then released into a living body to promote the growth and differentiation of cells. Therefore, in this case, the growth factor promotes the growth and differentiation of cells later as compared to a case where the organ regeneration device 1 carrying a growth factor is used.

In the case of using the organ regeneration device 1 carrying a recombinant plasmid (a growth-related nucleic acid), the recombinant plasmid is introduced into the cells of a living body. Then, a growth factor is produced in cells into which the recombinant plasmid has been introduced, and is then secreted outside the cells so that cells whose growth and differentiation is promoted by this growth factor are selectively grown and differentiated. Therefore, in this case, the growth factor promotes the growth and differentiation of cells later as compared to a case where the organ regeneration device 1 carrying host cells into which a growth-related nucleic acid has been introduced is used.

In the case of using the organ regeneration device 1 carrying a vector into which a recombinant plasmid (a growth-related nucleic acid) has been introduced, the recombinant plasmid is more smoothly introduced into the cells of a living body as compared to a case where the organ regeneration device 1 carrying a recombinant plasmid (a growth-related nucleic acid) is used. Therefore, in this case, a growth factor promotes the growth and differentiation of cells at timing intermediate between that achieved by the organ regeneration device 1 carrying a recombinant plasmid (a growth-related nucleic acid) and that achieved by the organ regeneration device 1 carrying host cells into which a growth-related nucleic acid has been introduced.

That is, the organ regeneration devices 1, ranked in order of the timing of promoting the growth and differentiation of cells by a growth factor from earliest to latest, are: the organ regeneration device 1 carrying a growth factor, the organ regeneration device 1 carrying host cells into which a growth-related nucleic acid has been introduced, the organ regeneration device 1 carrying a vector into which a growth-related nucleic acid has been introduced, and the organ regeneration device 1 carrying a growth-related nucleic acid (a recombinant plasmid). Therefore, the growth-related substance that should be contained in the organ regeneration device 1 can be selected from those described above according to the timing at which a growth factor should be secreted (supplied).

More specifically, in the case of a growth factor that should act on cells relatively early in the process of organ regeneration, it is preferred that the growth factor is directly carried on the organ regeneration device 1. Examples of such a growth factor include angiogenesis factors. When the organ regeneration device 1 carrying an angiogenesis factor as a growth factor is placed in a defective portion of skin, blood vessels are early regenerated during the regeneration of skin. Since blood vessels serve as pathways for supplying various substances and stem cells required for regeneration of organ tissue, new blood vessels are actively formed. Therefore, such substances and stem cells are efficiently supplied to a field of tissue regeneration so that organ regeneration is rapidly carried out.

On the other hand, in the case of a growth factor that should act on cells relatively late in the process of organ regeneration, the growth factor is preferably carried on the organ regeneration device 1 in the form of a host cell into which a growth-related nucleic acid has been introduced, a vector into which a growth-related nucleic acid has been introduced, or a growth-related nucleic acid (a recombinant plasmid). Examples of such a growth factor include growth factors involved in the regeneration of an appendage(s) of an organ.

In the case where the organ regeneration device 1 is used for regeneration of skin as described with reference to this embodiment, examples of such a growth factor include BMP and Wnt involved in the regeneration of pilosebaceous units.

This makes it possible to allow each growth factor to act on cells at its preferred timing so that an organ is restored to its normal state.

In view of the above, the timing and position at which the growth and differentiation of cells are promoted by a growth factor are determined by selecting, for example, the growth-related substance from a growth factor, a host cell into which a growth-related nucleic acid has been introduced, a vector into which a growth-related nucleic acid has been introduced, and a growth-related nucleic acid (a recombinant plasmid) and the position of a carrier for carrying the selected growth-related substance (either or both of the base body 2 and the particles 3). By doing so, it is possible to appropriately set the timing and position at which the growth and differentiation of cells are promoted by a growth factor. In the case where the organ regeneration device 1 according to the present invention is used for regeneration of a defective portion of skin as described with reference to this embodiment, it is preferred that an angiogenesis factor is carried on the base body 2 as a growth factor and host cells into which a nucleic acid containing a base sequence coding for the amino acid sequences of BMP and Wnt has been introduced are carried on the particles 3.

Hereinbelow, the process of regeneration of a defective portion of skin using, as the organ regeneration device 1 for regenerating defective skin, the above-mentioned one, that is, one in which an angiogenesis factor (e.g., bFGF) is carried on the base body 2 as a growth factor and host cells into which a nucleic acid containing a base sequence coding for the amino acid sequences of BMP and Wnt has been introduced are carried on the particles 3 will be described.

FIG. 4(a) to (d) are schematic diagrams for explaining the process of regenerating a defective portion of skin using the organ regeneration device 1 according to the present invention.

Figure 4:
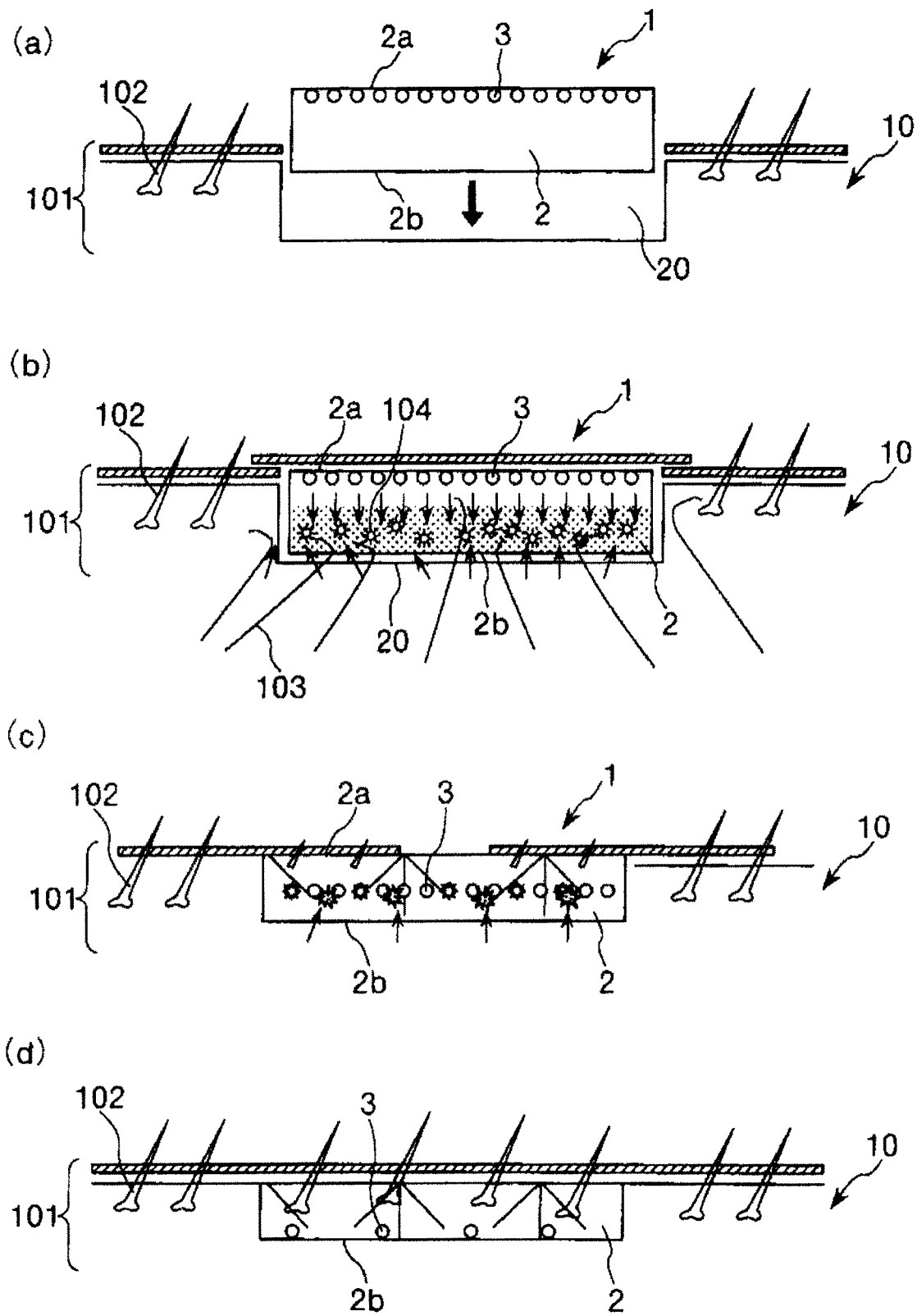
FIG. 4(a)-(d) is a schematic diagrams for explaining the process of regenerating a defective portion of skin using an organ regeneration device according to the present invention.

As shown in FIG. 4(a), skin 10 is mainly constituted from skin tissue 101 providing a body surface and pilosebaceous units 102 obliquely extending with respect to the thickness direction of the skin tissue 101. The pilosebaceous units 102 are spaced at almost equal intervals in the body surface.

A defective portion 20 of the skin 10 is regenerated using the organ regeneration device 1 in the following manner.

<C1> First, the organ regeneration device 1 is embedded (placed) in the defective portion 20 of the skin 10 so that the front face 2a of the base body 2 is located close to the body surface and the rear face 2b of the base body 2 is located close to the deep part of the skin 10 (see FIG. 4(a)).

When the organ regeneration device 1 is embedded in the defective portion 20 in such a manner as described above, as shown in FIG. 4(b), an angiogenesis factor carried on the base body 2 is released into a living body and the cells of the living body enter the inside of the base body 2. As a result, new blood vessels 103 are actively formed in the vicinity of the base body 2 and inside the base body 2 by cells whose growth and differentiation have been promoted by the angiogenesis factor. When the new blood vessels 103 are formed, substances and stem cells required for inducing the regeneration of the skin tissue 101 and the pilosebaceous units 102 are supplied through the blood vessels 103. As a result, the regeneration of the skin tissue 101 is induced, and then new skin 104 is formed from the edges of the defective portion.

<C2> Then, the particles 3 are gradually settled from the front face 2a side to the rear face 2b side of the base body 2 in the process of formation of the new skin 104. At this time, when Wnt and BMP are produced from the host cells carried on the particles 3, the growth and differentiation of stem cells required for inducing the regeneration of the pilosebaceous units 102 are promoted in this region (see FIG. 4(c)).

<C3> Then, when the growth and differentiation of stem cells are promoted, as shown in FIG. 4(d), the pilosebaceous units (appendages of skin) 102 each having a hair follicle, a sebaceous gland, etc. extend downwardly from the epidermis side to the dermis side so that the regeneration of the skin 10 proceeds.

It is to be noted that in the case where the base body 2 and the particles 3 contained in the organ regeneration device 1 are made of a bioabsorbable material as described above, they are gradually absorbed into a living body in the process of regeneration of skin and finally disappear.

In this way, the defective portion 20 is regenerated using the organ regeneration device 1 for the defective portion of the organ so that the skin 10 is restored to its normal state.

Hereinbelow, a method for producing the organ regeneration device 1 will be described with reference to a case where the organ regeneration device 1 having the above-described structure is produced.

<D1> First, host cells are allowed to adhere to the surfaces of the particles 3 and grown in a culture solution in the same manner as in the step <A1>.

<D2> Then, after the completion of the step <D1>, the culture solution in which the particles 3 to the surfaces of which the cells adhere are suspended is dropped into a Petri dish, and then the particles 3 are arranged on the bottom surface of the Petri dish so as not to be overlapped with each other.

Then, the base body 2 is placed on the particles 3 in such a manner that the flat surface of the base body 2 faces the particles 3 (i.e., faces the bottom surface of the Petri dish).

By doing so, the particles 3 penetrate the flat surface of the base body 2, and as a result, the base body 2 carrying the particles 3 in the vicinity of the front face 2a thereof can be obtained.

<D3> Then, a liquid in which an angiogenesis factor and a vector into which a recombinant plasmid having a base sequence coding for the amino acid sequences of growth factors (BMP and Wnt) inducing the regeneration of pilosebaceous units has been introduced are dissolved or suspended is prepared. The liquid is poured into the Petri dish in which the particles 3 and the base body 2 are contained, and then incubation is carried out.

As a result, it is possible to obtain an organ regeneration device 1 in which the angiogenesis factor is carried on the base body 2 and host cells into which a recombinant plasmid having a base sequence coding for the amino acid sequences of growth factors inducing the regeneration of pilosebaceous units has been introduced are carried on the particles 3.

The time for incubation is preferably in the range of about 0.2 to 5 hours, more preferably in the range of about 1 to 3 hours.

Although the preferred embodiment of the organ regeneration device according to the present invention has been described above, the present invention is not limited to this embodiment, and the structure of each component can be replaced with any structure having similar functions.

For example, in the above-described embodiment, cDNA has been described as a representative of a base sequence coding for the amino acid sequence of a growth factor, but such a base sequence may be, for example, mRNA corresponding to the amino acid sequence of a growth factor or one obtained by arbitrarily adding a base(s) to the mRNA.

EXAMPLES

Hereinbelow, actual examples of the present invention will be described.

Example 1

1. Preparation of Recombinant Plasmid

A BMP2-recombinant plasmid as shown in FIG. 2 was obtained by splicing BMP2 cDNA (a base sequence coding for BMP2) and desired base sequences into an expression plasmid by a well-known method.

Further, a Wnt-recombinant plasmid was obtained by splicing Wnt (human Wnt 3) cDNA (a base sequence coding for Wnt) into an expression plasmid as shown in FIG. 3, into which desired base sequences had been spliced, by a well-known method.

Then, each of the recombinant plasmids was grown in the following manner.

First, the recombinant plasmid was added to 200 μL of a suspension of DH5α (Competent Bacteria) at room temperature to obtain a mixture.

Then, the mixture was added to LB agar medium to carry out cultivation at 37° C. for 12 hours. Then, after the completion of the cultivation, a relatively large colony was selected from colonies grown on the LB agar medium, and was then inoculated on LB agar medium containing Amp (ampicillin) to further carry out cultivation at 37° C. for 12 hours.

Then, the cell membrane of the DH5α grown on the LB agar medium containing Amp was broken to obtain a solution, and then the recombinant plasmid was purified and separated from the solution.

2. Introduction of Recombinant Plasmid into Vector

Each of the Wnt-recombinant plasmid and BMP2-recombinant plasmid was introduced into an adenovirus by a well-known method.

3. Preparation of HAP Beads Carrying Cells

Hydroxyapatite was synthesized by a well-known wet synthesis method to obtain a slurry of hydroxyapatite. The slurry of hydroxyapatite was spray dried and then fired at 700° C. to obtain HAP beads (average particle size: 80 μm, specific area: about 20 $m^3/g$). The HAP beads and a suspension of fibroblasts were added to Dulbecco's MEM medium (a culture solution). It is to be noted that the Dulbecco's MEM medium used contained 10 vol % fetal bovine serum.

The Dulbecco's MEM medium was agitated at room temperature for 17 to 24 hours to culture fibroblasts.

After the completion of cultivation, the fibroblasts were stained with crystal violet to observe how the fibroblasts were attached to the HAP beads. As a result, it was found that the fibroblasts were grown (attached to the surface of the HAP beads) in such a manner that the surface of the HAP beads was covered with them.

4. Production of Organ Regeneration Device

First, 0.2 mL of the Dulbecco's MEM medium (a culture solution) in which the HAP beads (particles) were suspended was dropped into a 24-hole culture dish, and then about 50 HAP beads were arranged on the bottom surface of each hole in such a manner that the HAP beads were not overlapped with each other.

Then, a disk-shaped collagen sponge ("Terdermis", Terumo Corporation, pore size: about 200 μm, diameter: 10 mm, thickness: 3 mm) was placed on the particles in each hole of the culture dish in such a manner that the flat surface thereof faced the particles.

As a result, the HAP beads penetrated the flat surface of the collagen sponge (base body) so that the collagen sponge carrying the HAP beads in the vicinity of the surface thereof was obtained.

Then, 0.1 mL of a 10 μg/mL bFGF solution, 0.2 mL of a suspension containing the Wnt-recombinant plasmid introduced into an adenovirus vector, and 0.2 mL of a suspension containing the BMP 2-recombinant plasmid introduced into an adenovirus vector were poured into each hole of the culture dish containing the particles and the base body. Then, incubation was carried out using a $CO_2$ incubator for 1 hour.

As a result, bFGF, the Wnt-recombinant plasmid, and the BMP 2-recombinant plasmid permeated the collagen sponge so that bFGF was carried on the collagen sponge (base body) and the Wnt-recombinant plasmid and the BMP 2-recombinant plasmid were introduced into the fibroblasts carried on the surfaces of the particles.

Example 2

An organ regeneration device was produced in the same manner as in the Example 1 except that in the step of producing an organ regeneration device, 0.2 mL of the culture solution was poured into each hole of the culture dish containing the particles and the base body instead of the suspension containing the BMP 2-recombinant plasmid introduced into an adenovirus vector.

Example 3

An organ regeneration device was produced in the same manner as in the Example 1 except that in the step of producing an organ regeneration device, 0.2 mL of the culture solution was poured into each hole of the culture dish containing the particles and the base body instead of the suspension containing the Wnt-recombinant plasmid introduced into an adenovirus vector.

Example 4

An organ regeneration device was produced in the same manner as in the Example 1 except that in the step of producing an organ regeneration device, 0.4 mL of the culture solution was poured into each hole of the culture dish containing the particles and the base body instead of the suspension containing the Wnt-recombinant plasmid introduced into an adenovirus vector and the suspension containing the BMP 2-recombinant plasmid introduced into an adenovirus vector.

In this way, the organ regeneration devices of the Examples 1 to 4 were obtained.

<Evaluation>

1. Evaluation Experiment

Figure 5:
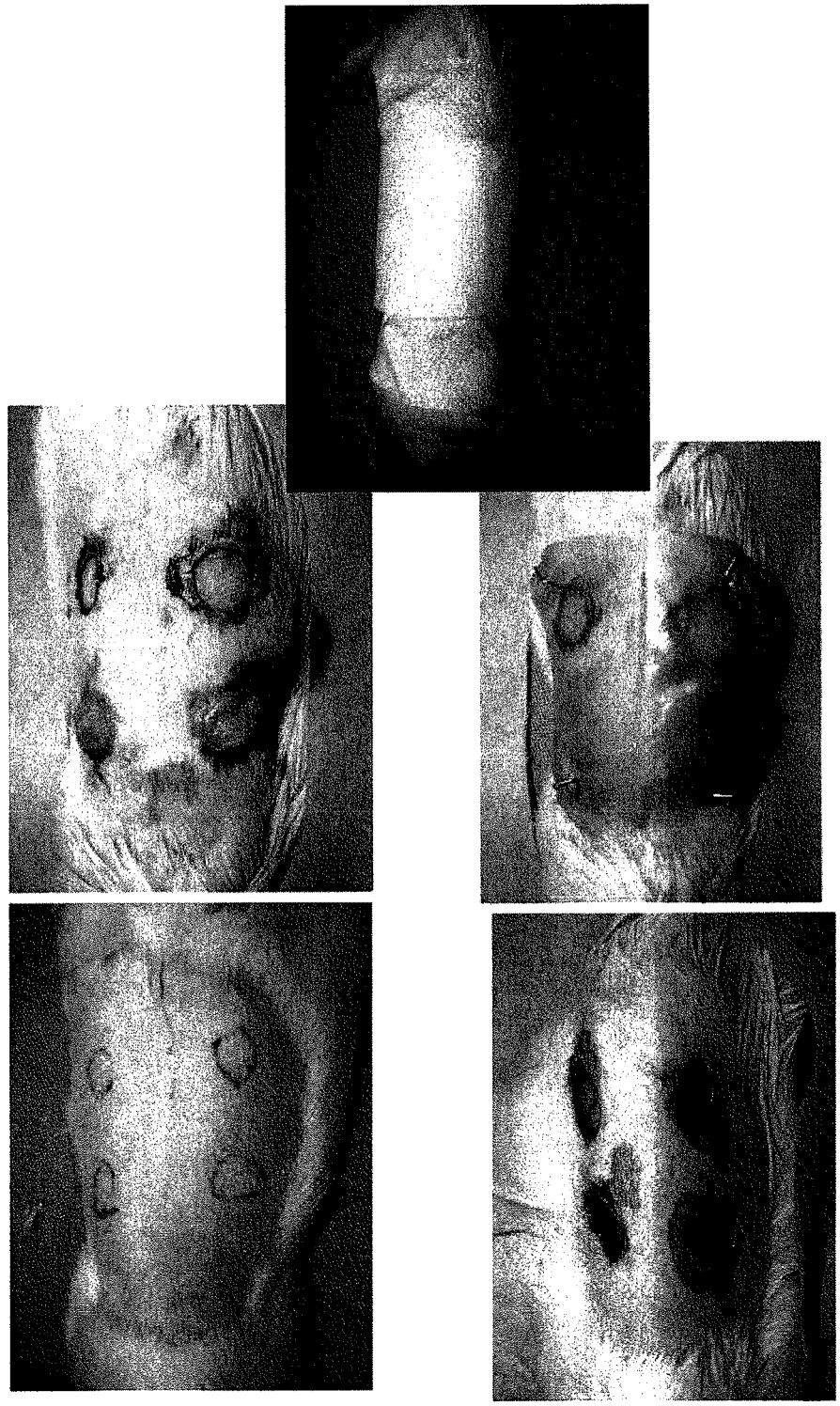
FIG. 5 shows photographs for explaining a surgical procedure performed on rats.

First, 5 rats were prepared, and then each of the rats was subjected to a surgical procedure in the following manner (see FIG. 5).

Each of the rats was intraperitoneally anesthetized, and then the dorsal hair of the rat was shaved and full-thickness skin was removed at 4 positions in its dorsal region with no hair using a skin puncher having a diameter of 8 mm so that tunica dartos was exposed, thereby forming four defective portions.

Then, bleeding from the defective portions from which skin had been removed was stopped, and then the organ regeneration devices produced in the Examples 1 to 4 were embedded in and fixed to the four defective portions, respectively.

Then, the organ regeneration devices fixed to the defective portions were covered with Absocure Surgical and further fixed using a skin stapler and a tape. Then, these rats subjected to such a surgical procedure as described above were bred in their respective cages.

2. Evaluation Result

These rats were killed by an overdose of an anesthetic at the 2nd, 4th, 8th, 12th, and 16th week after the surgical procedure.

Then, tissue was sampled from each of the defective portions to prepare a tissue specimen.

An image of each of the tissue specimens was taken with a stereoscopic microscope system SZX-12 (manufactured by Olympus) equipped with a digital camera (DP-12) to observe the process of regeneration of skin.

Figure 6:
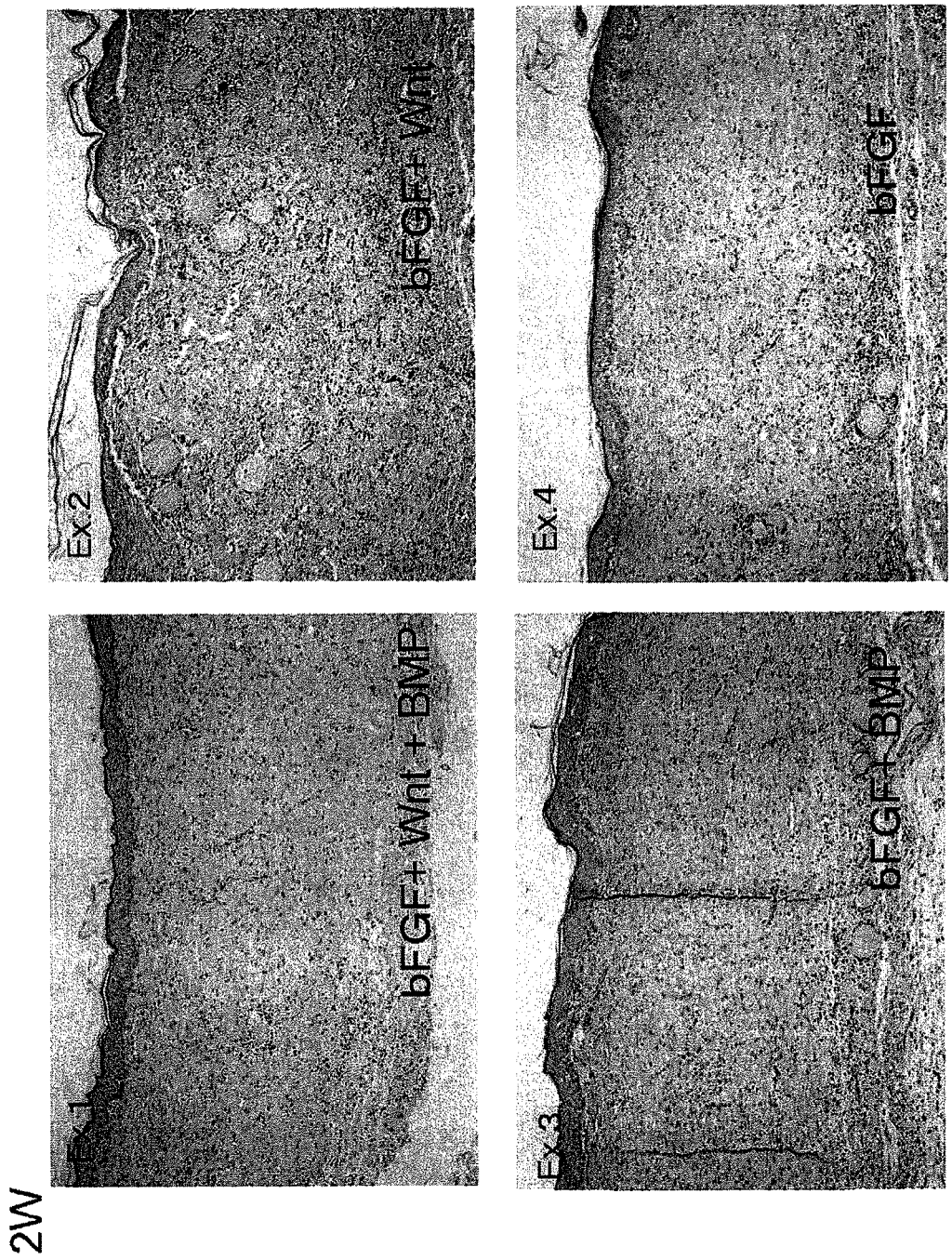
FIG. 6 shows stereomicroscope photographs showing the conditions of defective portions of skin at the 2nd week after embedding organ regeneration devices of Examples 1 to 4 in the defective portions.
Figure 7:
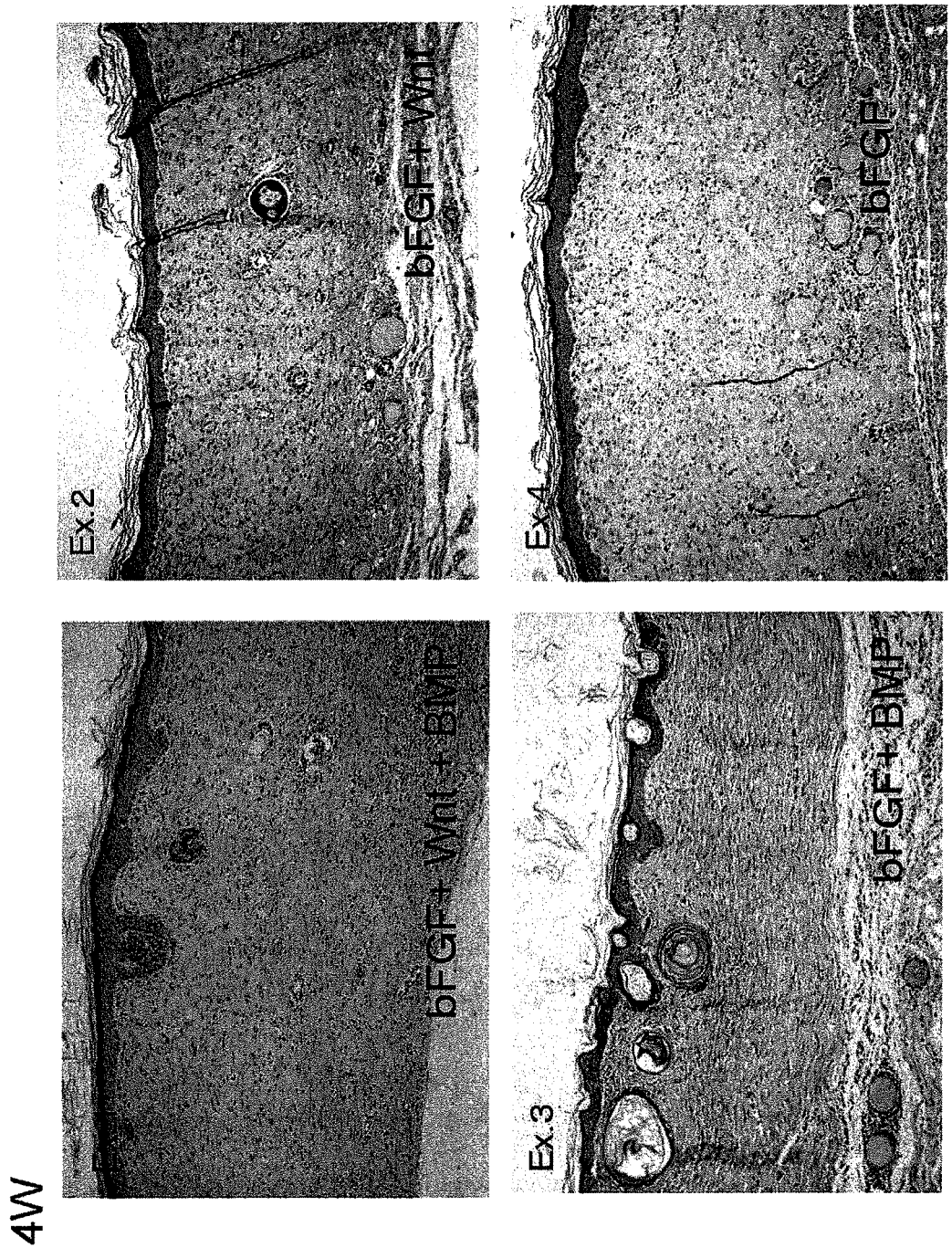
FIG. 7 shows stereomicroscope photographs showing the conditions of defective portions of skin at the 4th week after embedding organ regeneration devices of Examples 1 to 4 in the defective portions.

As a result, as shown in FIGS. 6 and 7, epithelialization from the edges of a defective portion was completed at the 4th week in all the defective portions in which the organ regeneration devices of the Examples 1 to 4 had been implanted, respectively.

Figure 8:
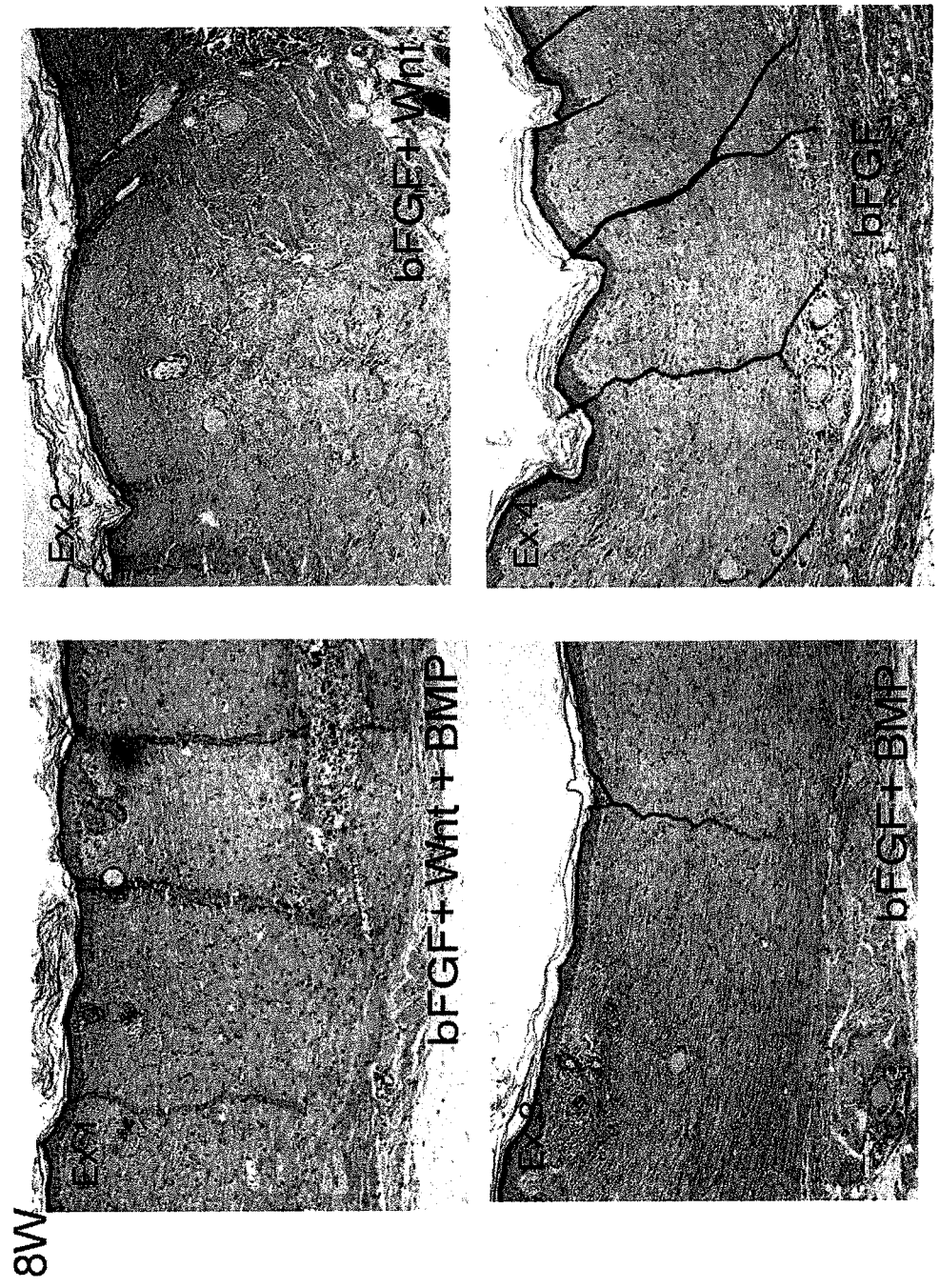
FIG. 8 shows stereomicroscope photographs showing the conditions of defective portions of skin at the 8th week after embedding organ regeneration devices of Examples 1 to 4 in the defective portions.
Figure 9:
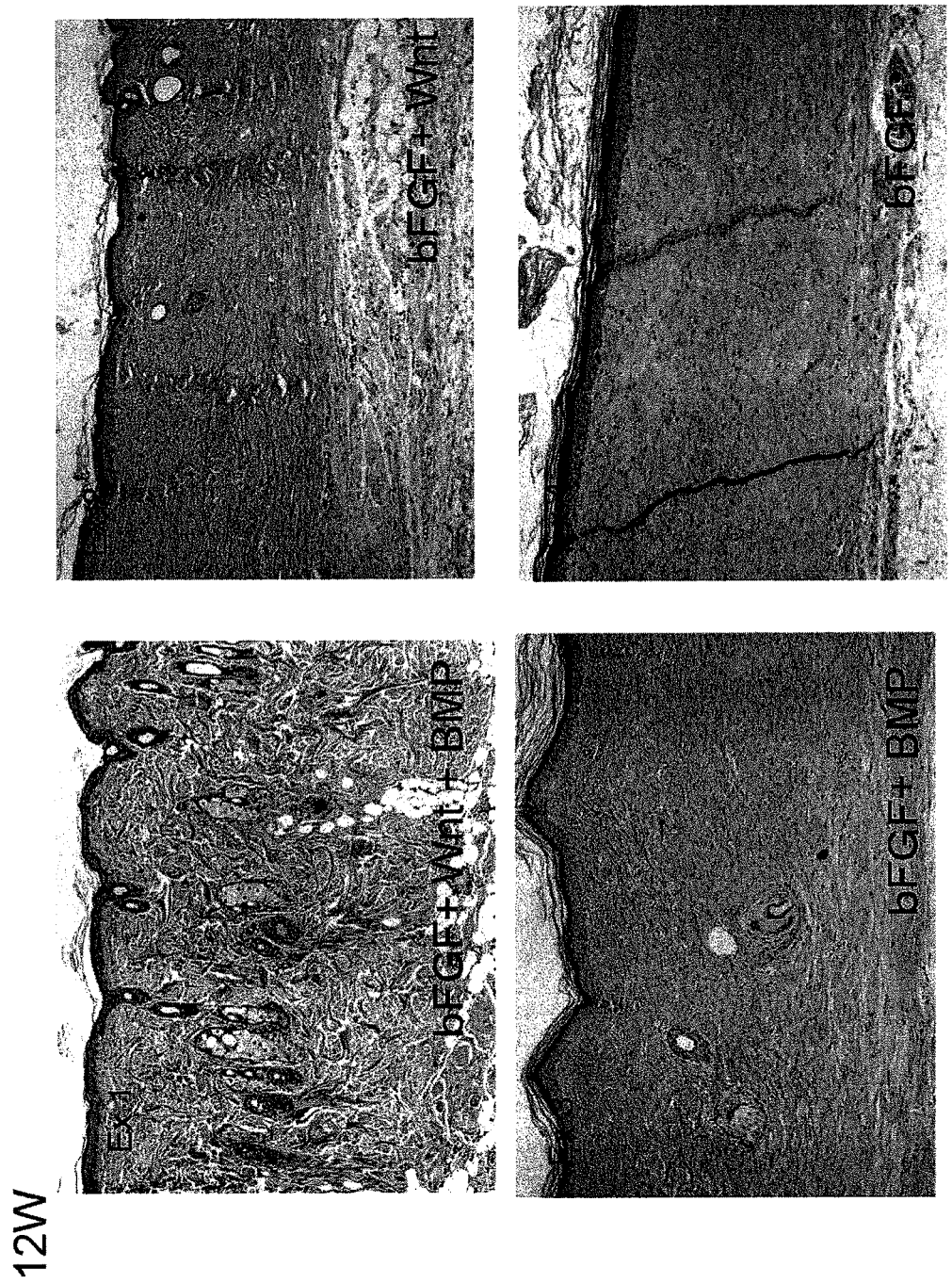
FIG. 9 shows stereomicroscope photographs showing the conditions of defective portions of skin at the 12th week after embedding organ regeneration devices of Examples 1 to 4 in the defective portions.
Figure 10:
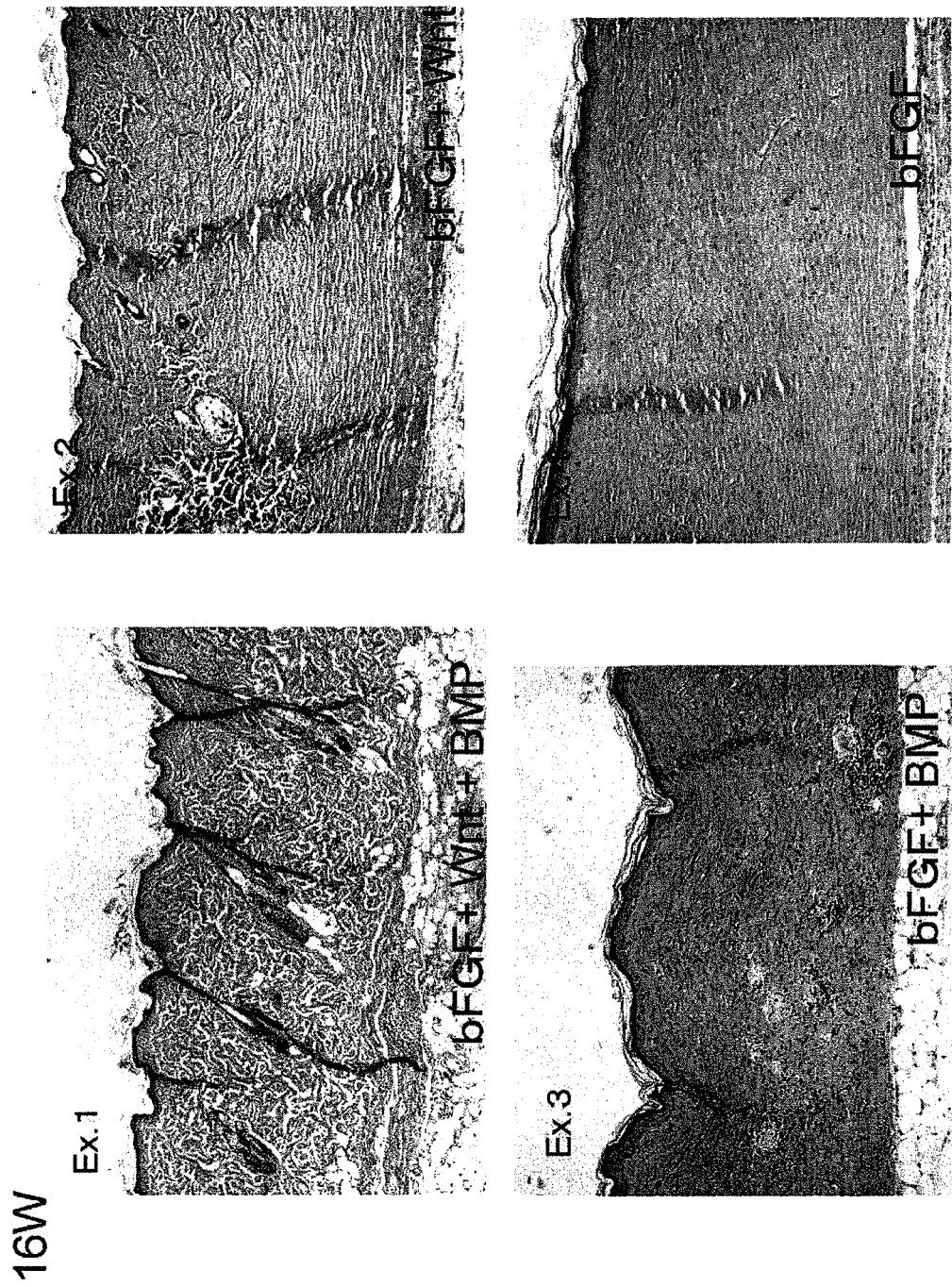
FIG. 10 shows stereomicroscope photographs showing the conditions of defective portions of skin at the 16th week after embedding organ regeneration devices of Examples 1 to 4 in the defective portions.

Among these defective portions, in the defective portion in which the organ regeneration device of the Example 1 had been implanted, the appearance of follicle germ or primitive hair germ was observed at the 4th week, and elongation of follicular pegs into the dermis and formation of hair shafts were observed after about the 8th week. Further, from about the 8th week to the 12th week, formation of sebaceous glands was observed (see FIGS. 7 to 9). At this time, maturer hair follicles were present closer to the edges of the defective portion. This suggests that epithelialization starts from the edges of the defective portion of skin and then hair follicles are formed. Then, at the 16th week, the formation of skin having mature pilosebaceous units in the defective portion was observed (see FIG. 10). These pilosebaceous units were spaced at equal intervals (about 300 μm) and inclined with respect to a body surface similarly to those in normal skin.

In the defective portions in which the organ regeneration devices not carrying BMP 2 and/or Wnt (Examples 2 to 4) had been implanted, regeneration of pilosebaceous units was observed, but as can be seen from the conditions of the defective portions at the 16th week, regeneration of skin was incomplete as compared to a case where the organ regeneration device of the Example 1 was implanted.

From these results, it has become apparent that a combination use of an angiogenesis factor, BMP 2, and Wnt makes it possible to restore skin to its normal state. More specifically, it has become apparent that skin regeneration can be more reliably performed by allowing the base body to directly carry an angiogenesis factor in the form of protein and by allowing the particles to carry host cells into which a nucleic acid having a base sequence coding for the amino acid sequences of BMP 2 and Wnt has been introduced so that BMP 2 and Wnt can be produced in these host cells.

Finally it is to be understood that the present disclosure relates to the subject matter contained in Japanese Patent Application No. 2007-311777 (filed on Nov. 30, 2007) which is expressly incorporated herein by reference in its entirety.

What is claimed is:

1. An organ regeneration device for regenerating a defective portion of an organ, the organ regeneration device being adapted to be used by placing it into the defective portion, comprising:

a base body having a front face, a rear face opposite to the front face and a shape corresponding to a shape of the defective portion of the organ, and the base body having a thickness direction from the front face to the rear face, the base body being a bioabsorbable material;

particles composed of a different material from that of the base body; and a first growth-related substance contained in the organ regeneration device for growth and differentiation of cells around the defective portion, the first growth-related substance carried on the base body, wherein at least a part of each of the particles has penetrated the surface of the front face of the base body or the rear face of the base body so as not to be overlapped with each other in the thickness direction of the base body, the organ is constituted of an ectodermal tissue and an endodermal tissue being in contact with the ectodermal tissue, and the first growth-related substance contains at least one of an angiogenesis factor and a first nucleic acid containing a base sequence coding for amino-acid sequence of the angiogenesis factor.

2. The organ regeneration device as claimed in claim 1, wherein the base body has a three-dimensional network structure.

3. The organ regeneration device as claimed in claim 1, wherein at least a surface of each of the particles contains a calcium phosphate-based compound as a major component thereof.

4. The organ regeneration device as claimed in claim 3, wherein the calcium phosphate-based compound contains hydroxyapatite as a major component thereof.

5. The organ regeneration device as claimed in claim 1, wherein the average particle size of the particles is 50 to 1000 μm.

6. The organ regeneration device as claimed in claim 1, wherein the porosity of the particles is in the range of 10 to 75%.

7. The organ regeneration device as claimed in claim 1, wherein the growth-related substance contains at least one of a growth factor different from the angiogenesis factor and nucleic acid containing a base sequence coding for amino-acid sequence of the growth factor.

8. The organ regeneration device as claimed in claim 7, wherein at least one of the growth factor and the nucleic acid containing a base sequence coding for amino-acid sequence of the growth factor is directly or indirectly adsorbed to the particles.

9. The organ regeneration device as claimed in claim 8, wherein the nucleic acid is recombinant plasmid containing a base sequence derived from an expression plasmid, in which the expression plasmid is directly adsorbed to the particles.

10. The organ regeneration device as claimed in claim 9, further comprising a vector, wherein the vector is adsorbed to the particles, and the nucleic acid is introduced into the vector.

11. The organ regeneration device as claimed in claim 10, wherein the vector is derived from a non-virus.

12. The organ regeneration device as claimed in claim 11, further comprising a host cell, wherein the host cell is adsorbed to the particles, and the nucleic acid is introduced into the host cell.

13. The organ regeneration device as claimed in claim 1, wherein the organ is skin.

14. The organ regeneration device as claimed in claim 7, wherein the growth factor is at least one of Wingless int 3 (Wnt) and bone morphogenetic protein (BMP).

15. The organ regeneration device as claimed in claim 3, wherein each of the particles has an inner part covered with the surface, the inner part of the particle is formed from a substrate mainly made of a resin material.

16. The organ regeneration device as claimed in claim 1, an average particle size of the particles is smaller than a thickness of the base body.

17. The organ regeneration device as claimed in claim 1, wherein all of the particles are fully penetrated in the surface of the front face of the base body or the rear face of the base body.

18. The organ regeneration device as claimed in claim 1, wherein the bioabsorbable material is a collagen sponge made of soluble collagen.

19. The organ regeneration device as claimed in claim 1, wherein the ectodermal tissue is an epithelium and the endodermal tissue is a dermis.

20. The organ regeneration device as claimed in claim 1, wherein the angiogenesis factor is at least one selected from the group consisting of basic Fibroblast Growth Factor (bFGF), Vascular Endothelial Growth Factor (VEGF), and Hepatocyte Growth Factor (HGF).

21. The organ regeneration device as claimed in claim 1, wherein the organ regeneration device further comprises a second growth-related substance carried on the particles, and the second growth-related substance contains at least one of a morphogen and a second nucleic acid containing a base sequence coding for amino-acid sequence of the morphogen.

22. The organ regeneration device as claimed in claim 18, wherein the porosity of the collagen sponge is in the range of 30 to 95%.

* * * * *